(12) United States Patent
Kaplan et al.

(10) Patent No.: US 12,331,313 B2
(45) Date of Patent: Jun. 17, 2025

(54) TUNABLE SILK-BASED BIOMATERIALS WITH SACCHARIDE SUBSTITUTIONS, AND METHODS OF PRODUCING THE SAME

(71) Applicant: Trustees of Tufts College, Medford, MA (US)

(72) Inventors: David L. Kaplan, Concord, MA (US); Jugal Kishore Sahoo, Belmont, MA (US); Onur Hasturk, Medford, MA (US); Jaewon Choi, Cambridge, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 18/352,366

(22) Filed: Jul. 14, 2023

(65) Prior Publication Data
US 2024/0132836 A1 Apr. 25, 2024

Related U.S. Application Data

(63) Continuation of application No. PCT/US2022/070215, filed on Jan. 17, 2022.

(60) Provisional application No. 63/138,193, filed on Jan. 15, 2021.

(51) Int. Cl.
| | | |
|---|---|---|
| *C07K 14/435* | (2006.01) | |
| *A61L 27/36* | (2006.01) | |
| *C12N 5/00* | (2006.01) | |
| *A61L 27/52* | (2006.01) | |
| *A61L 27/56* | (2006.01) | |

(52) U.S. Cl.
CPC ........ *C12N 5/0068* (2013.01); *A61L 27/3604* (2013.01); *C07K 14/43586* (2013.01); *A61L 27/52* (2013.01); *A61L 27/56* (2013.01); *C12N 2533/50* (2013.01); *C12N 2537/10* (2013.01)

(58) Field of Classification Search
CPC .................. C07K 14/43586; C12N 2537/10
See application file for complete search history.

(56) References Cited

U.S. PATENT DOCUMENTS

| | | | |
|---|---|---|---|
| 2006/0205927 A1 | 9/2006 | Jin et al. | |
| 2011/0027890 A1 | 2/2011 | Fujita et al. | |
| 2014/0315828 A1* | 10/2014 | Pavlovic | C08J 3/246 |
| | | | 530/353 |
| 2015/0342854 A1 | 12/2015 | Shibuya et al. | |
| 2018/0050109 A1 | 2/2018 | Kaplan et al. | |
| 2023/0114250 A1* | 4/2023 | Altman | A61K 8/735 |
| | | | 424/428 |

FOREIGN PATENT DOCUMENTS

WO 2022155682 A1 7/2022

OTHER PUBLICATIONS

Murphy et al., J. Mater. Chem., 2009, vol. 19(36):6443-6450.*
UniProt, Entry Q7JYG3, fibroin light chain of Bombyx Mori (sequence last updated Jul. 5, 2004).*
Esko, Jeffrey D., et al., "Animal Cell mutants defective in glycosaminoglycan biosynthesis", Proc. Natl. Acad. Sci. USA, 1985, vol. 82(10):3197-3201.
PCT/US2022/070215, "International Application Serial No. PCT/US2022/070215, International Preliminary Report on Patentability mailed Jul. 27, 2023", Tufts University, 8 pages.
PCT/US2022/070215, "International Application Serial No. PCT/US2022/070215, International Search Report and Written Opinion mailed May 18, 2022", Tufts University, 10 pages.
PCT/US2022/070215, "International Application Serial No. PCT/US2022/070215, Preliminary Report on Patentability mailed Jul. 27, 2023", Tufts University, 10 pages.

* cited by examiner

*Primary Examiner* — Xiaozhen Xie
(74) *Attorney, Agent, or Firm* — GTC Law Group PC & Affiliates

(57) ABSTRACT

Saccharide-substituted silk fibroin compositions as well as methods for making and using the same are provided. The compositions can include at least one saccharide coupled to silk fibroin. The coupling can be via various residues on the silk fibroin.

18 Claims, 19 Drawing Sheets

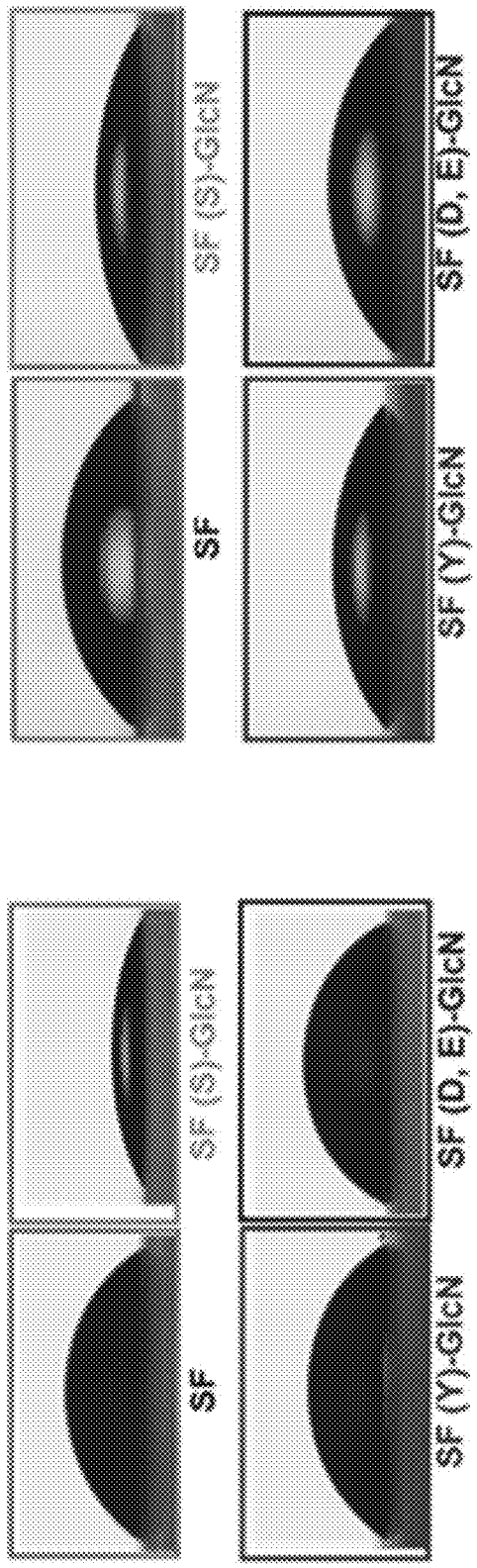
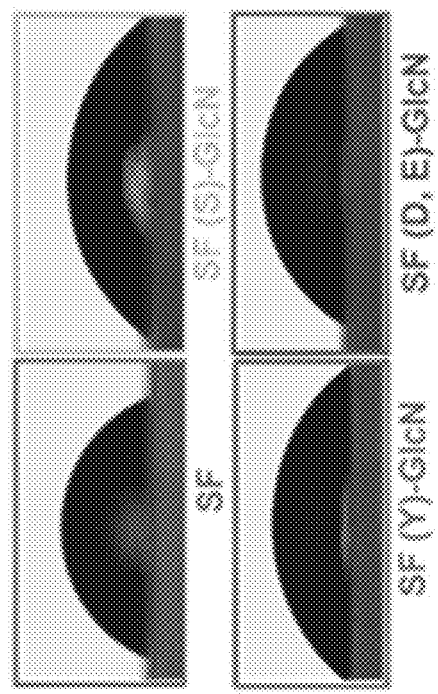
FIG. 4A
FIG. 4B

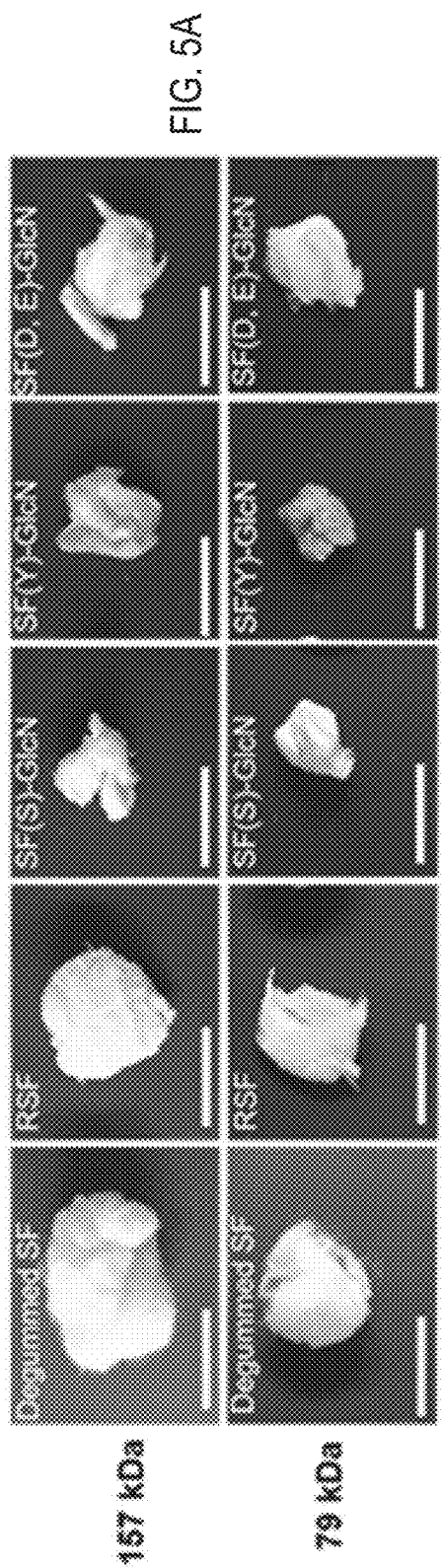
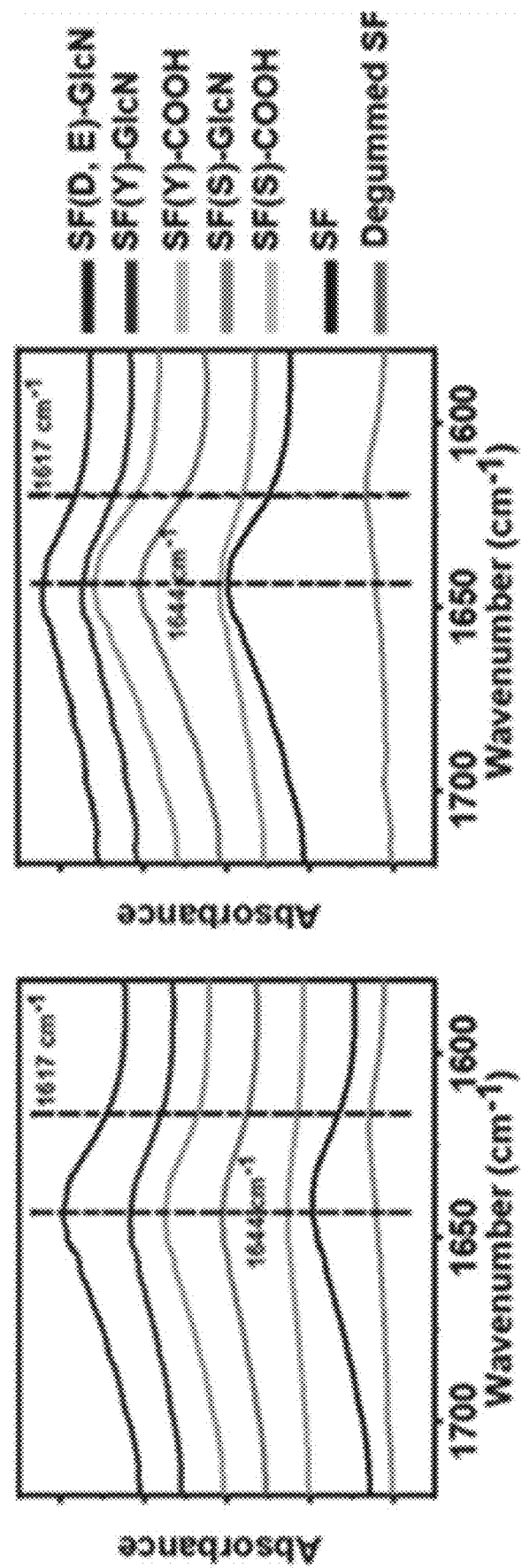
FIG. 5A
FIG. 5B
FIG. 5C

TUNABLE SILK-BASED BIOMATERIALS WITH SACCHARIDE SUBSTITUTIONS, AND METHODS OF PRODUCING THE SAME

CROSS-REFERENCE TO RELATED APPLICATIONS

This application is a bypass continuation of International Application Serial Number PCT/US2022/070215, filed Jan. 17, 2022 (2095.0445). International Application Serial Number PCT/US2022/070215 is related to, claims priority to, and incorporates herein by reference for all purposes U.S. Provisional Patent Application No. 63/138,193, filed Jan. 15, 2021 (2095.0444). Each of the foregoing patent applications is incorporated herein by reference in their entirety for all purposes.

STATEMENT REGARDING FEDERALLY SPONSORED RESEARCH

This invention was made with government support under grants EB002520 and EB027062 awarded by the National Institutes of Health and FA9950-17-1-0333 awarded by the United States Air Force. The government has certain rights in the invention.

BACKGROUND

Silk fibroin (SF), a natural protein-based biopolymer from cocoons of *Bombyx mori* silkworms, has been widely applied for a broad range of biomedical applications and has found utility in biomaterials and regenerative medicine.[1-3] Silk biomaterials provide many useful features such as robust mechanical properties, biocompatibility, controlled biodegradability and aqueous-processability.[4-5] The strong mechanical properties can be attributed to the formation of β-sheet crystals, composed of repetitive sequences of glycine, alanine and serine.[6-7] In addition, silk biomaterials have been extensively applied in different fields of biomedicine as sutures,[3] matrices for drug-delivery[8] and as scaffolds for tissue engineering.[9-11] These properties make silk biomaterials outstanding candidates for applications in medicine in different material formats such as films,[12-13] hydrogels,[14-17] sponges,[18-20] and membranes.[21-22] In some applications, SF scaffolds benefit from chemical modification to modulate cell-adhesion and growth and to impact biochemical pathways.[23-24] Chemical modification of SF can also enhance physicochemical properties, improve materials tunability towards biological functions, and can be leveraged for a desired application.[1]

Sugars serve as one of the structural components of the extracellular matrix, as energy sources and as a key component in molecular recognition,[25] including roles in cell adhesion, differentiation, regulation and many different intracellular communication and signal transduction events.[25-26] Sugars also influence cell-material interactions facilitated by glycoproteins present on cell membranes. Typically, sugars, glycated proteins, and lipids bind to lectins on cell surfaces and facilitate interactions.[25] Silk-sugar conjugates can act as glycosaminoglycans (GAGs) mimics. GAGs are long chain, linear polysaccharides with repeat disaccharide units present in connective tissues, extracellular matrices (ECM) and on cell-surfaces as signaling molecules.[27] Because of their multiple regulatory roles, sugars are utilized in different biomedical applications such as the anticoagulation of blood, as anti-inflammatory components and as anti-tumor agents.[27] In addition, GAGs are also used as coating materials for implants, and as components for 3D scaffolds for tissue engineering.[27]

SUMMARY OF THE INVENTION

In one aspect, provided herein is a composition comprising saccharide-substituted silk fibroin. The saccharide-substituted silk fibroin comprises at least one saccharide is coupled to silk fibroin via a serine residue on the silk fibroin.

In another aspect, provided herein is a method for producing saccharide-substituted silk fibroin. The method comprises coupling a saccharide to silk fibroin within a silk fibroin solution to produce the saccharide-substituted silk fibroin, where the saccharide is coupled to the silk fibroin via a serine residue.

In one aspect, provided herein is a composition comprising saccharide-substituted silk fibroin. The saccharide-substituted silk fibroin comprises at least one saccharide coupled to silk fibroin via an aspartic acid residue on the silk fibroin, and at least one saccharide coupled to the silk fibroin via a glutamic acid residue on the silk fibroin.

In another aspect, provided herein is a method for producing saccharide-substituted silk fibroin. The method comprises coupling a saccharide to silk fibroin within a silk solution to produce the saccharide-substituted silk fibroin, where the saccharide is coupled to the silk fibroin via an aspartic acid reside and a glutamic acid residue.

In one aspect, provided herein is a composition comprising saccharide-substituted silk fibroin. The saccharide-substituted silk fibroin comprises at least one saccharide coupled to silk fibroin via a tyrosine residue on the silk fibroin.

In another aspect, provided herein is a method for producing saccharide-substituted silk fibroin. The method comprises coupling a saccharide to silk fibroin within a silk fibroin solution to produce the saccharide-substituted silk fibroin, wherein the saccharide is coupled to the silk fibroin via a tyrosine residue.

BRIEF DESCRIPTION OF DRAWINGS

The patent or patent application file contains at least one drawing in color. Copies of this patent or patent application publication with color drawings will be provided by the Office upon request and payment of the necessary fee.

FIG. 4A shows water contact angle (WCA) measurements of as cast SF-GlcN films prepared from SF-GlcN lyophilized powders from different modification pathways in accordance with some embodiments of the present disclosure. WCA images of as cast films of SF and GlcN functionalized SF in different synthetic pathways, as labeled. Left and right-side images are WCA of SF and different SF-GlcN films prepared from regenerated SF of MW 157 and 79 kDa respectively.

FIG. 4B shows WCA measurements of methanol treated SF-GlcN films prepared from SF-GlcN lyophilized powders from different modification pathways in accordance with some embodiments of the present disclosure. WCA images of methanol treated films of SF and GlcN functionalized SF in different synthetic pathways, as labeled. Left and right quartets of images are WCA of SF and different SF-GlcN films prepared from regenerated

FIG. 5A shows digital images of degummed SF, lyophilized regenerated SF and SF-GlcN in different synthetic pathways. Scale bar: 1 cm.

FIG. 5B shows FT-IR spectra of degummed SF, regenerated SF, SF-GlcN powders synthesized in different chemical pathways, and the reaction intermediates in each pathway starting from 157 kDa. The plots are vertically aligned in the same order as the legend of FIG. 5C. Degummed SF (157, bottom line) exhibits strong absorption peak at 1617 $cm^{-1}$ indicating secondary structure related to β-sheet configuration. All other samples including regenerated SF, reaction intermediates (SF(S)—COOH and SF(Y)—COOH in Pathway 1 and 2) and SF-GlcN prepared in each pathway exhibit strong absorption peak at 1644 $cm^{-1}$ indicating random coil structure.

FIG. 5C shows FT-IR spectra of degummed SF, regenerated SF, SF-GlcN powders synthesized in different chemical pathways, and the reaction intermediates in each pathway starting from 79 kDa MW SF. The plots are vertically aligned in the same order as the legend. Degummed SF (79 kDa; bottom line) exhibits strong absorption peak at 1617 $cm^{-1}$ indicating secondary structure related to β-sheet configuration. All other samples including regenerated SF, reaction intermediates (SF(S)—COOH and SF(Y)—COOH in Pathway 1 and 2) and SF-GlcN prepared in each pathway exhibit strong absorption peak at 1644 $cm^{-1}$ indicating random coil structure.

INCORPORATION BY REFERENCE

Figure 1:
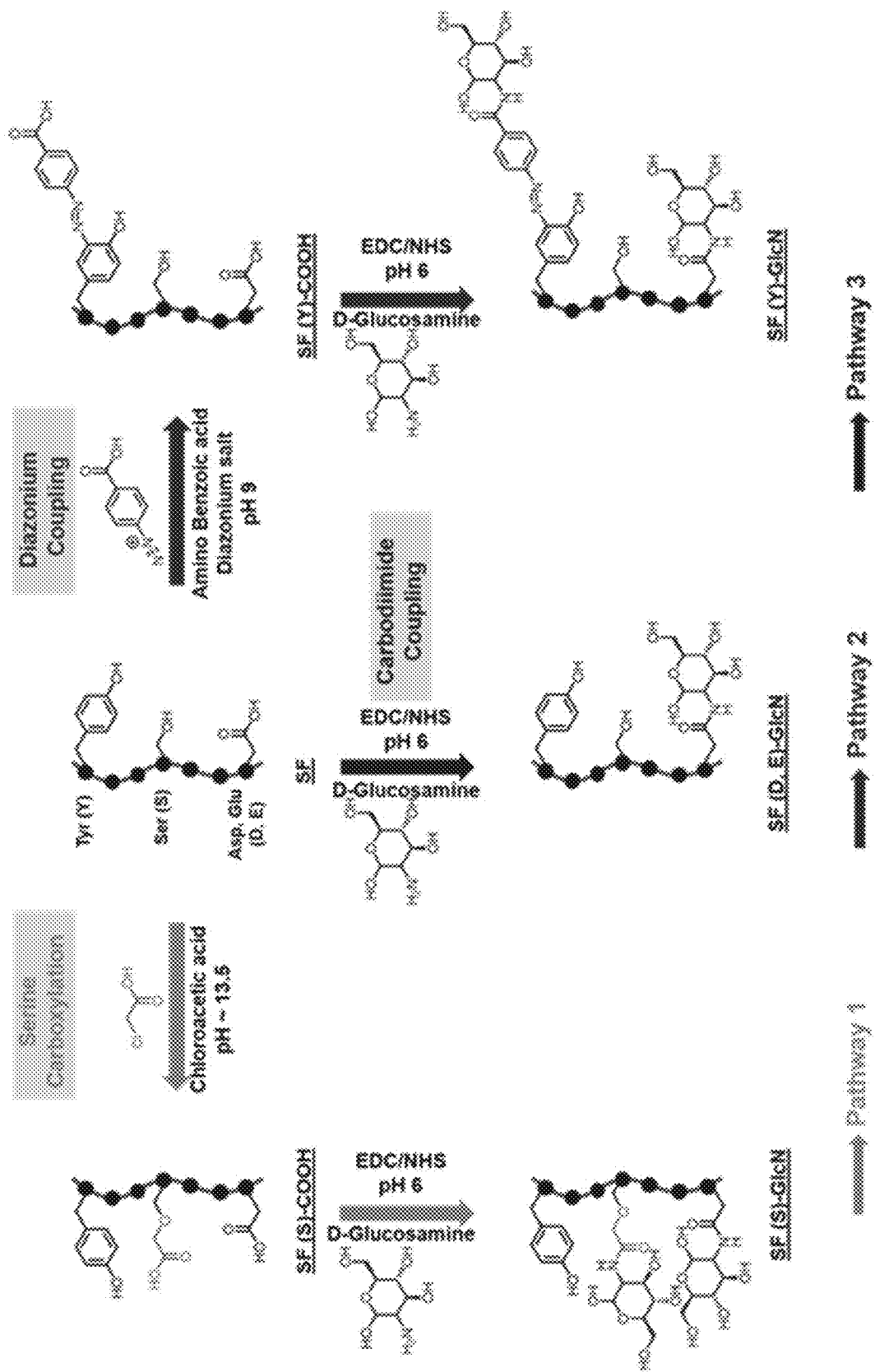
FIG. 1 shows a schematic representation of reaction pathways for modifying silk fibroin with saccharides in accordance with some embodiments of the present disclosure. Pathway 1 shows carboxylation of serine (S) residues in silk fibroin, followed by carbodiimide coupling with a saccharide (e.g., D-(+)-glucosamine) in the presence of EDC/NHS in a buffered solution. Pathway 2 shows carboxylation of tyrosine (Y) via diazonium coupling in a buffered solution, followed by carbodiimide coupling with a saccharide in the presence of EDC/NHS. Pathway 3 shows direct carbodiimide coupling by EDC/NHS of aspartic and glutamic acid (D, E) residues with a saccharide.

All publications, patents, and patent applications mentioned in this specification are herein incorporated by reference to the same extent as if each individual publication, patent, and patent application was specifically and individually indicated to be incorporated by reference.

DETAILED DESCRIPTION OF THE INVENTION

In order for the present disclosure to be more readily understood, certain terms are first defined below. Additional definitions for the following terms and other terms are set forth throughout the specification.

In this application, unless otherwise clear from context, the term "a" may be understood to mean "at least one." As used in this application, the term "or" may be understood to mean "and/or." In this application, the terms "comprising" and "including" may be understood to encompass itemized components or steps whether presented by themselves or together with one or more additional components or steps. Unless otherwise stated, the terms "about" and "approximately" may be understood to permit standard variation as would be understood by those of ordinary skill in the art. Where ranges are provided herein, the endpoints are included. As used in this application, the term "comprise" and variations of the term, such as "comprising" and "comprises," are not intended to exclude other additives, components, integers or steps.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

The present disclosure provides methods to produce compositions composed of silk fibroin-based biomaterials with different saccharide molecules using multiple chemistries in a covalent fashion. The methods for producing the provided compositions are simple, robust and can be generalized across different molecular weights of silk, and different saccharide moieties. The provided methods and compositions are applicable to an myriad of applications, including but not limited to brain ECM substitutes, cartilage matrices for repair, vitreous substitutions, lubricants in joints and many other areas of utility, where biological substitutes are needed with relatively slow degradation rates would be advantageous, and where drug loading and delivery could be combined with the provided compositions.

In some embodiments, the provided compositions reduce cell attachment and growth on a surface of the provided compositions, revealing anti-adhesive properties with respect to cells. The provided silk fibroin-based compositions (and other natural biopolymers such as silk-elastin like polymer (SELPs)) offer applications in a broad range of biomedical needs as anti-adhesive materials, mimics of complex tissue systems, and as drug delivery matrices, among others. In addition, natural biopolymers modified with sugars could offer unique opportunities to generate surface features with control over biofouling as biomimetic coating materials.

The provided methods and compositions offer various advantages. For example, the provided chemical functionalization strategy to introduce saccharides onto silk fibroin (here silk fibroin refers to any silk—e.g., fibroin, spidroin, genetic variants etc.) involves a green approach, i.e., the reaction steps of the saccharide modifications on silk fibroin may occur in aqueous solvents/buffers, thus avoiding use of organic solvents or harsh reaction conditions. The provided methods offer different chemistries to modify silk fibroin. Described in the present disclosure are specific and targeted, e.g., different reaction pathways/chemistries that target specific amino acids in the silk fibroin backbone for modification are addressed related to control of material properties, degree of substitution and overall impact on solubility or properties. The various approaches provided herein facilitate multiple saccharide substitutions with control on a silk protein chain, due to the selectivity in chemistries available.

The provided methods and compositions are robust, i.e., the provided methods can be implemented across different molecular weights and types of silk and can also be applied to covalently conjugate different saccharide molecules (e.g., monosaccharides, disaccharides, oligosaccharides, polysaccharides, and a combination thereof). Additionally, the provided methods have facile conjugation and purification, allowing the provided methods and compositions to be scaled up as needed. The provided methods and compositions having silk fibroin substituted with at least one saccharide residue is tunable depending on the chemistry used for conjugation. Different chemistries enable different saccharide substitutions and related single or multiple functionalization of the silk fibroin. The provided methods and compositions allow for the saccharide substituted silk fibroin to be processed into different functional material formats such as hydrogels, sponges, films, particles, fibers, etc. via controlling different processing parameters such as silk molecular weight, weight percent of the materials and temperature, along with the nature of the sugars appended on the chains. The provided compositions having saccharide substituted silk fibroin, depending on the chemistry used for modification, may be selectively tuned to have a desired water contact angle (surface hydrophobicity) and/or β-sheet content, thus, permitting tailorable material surface properties, and biological interactions.

Silk is a natural protein fiber produced in a specialized gland of certain organisms. Silk production in organisms is especially common in the Hymenoptera (bees, wasps, and ants), and is sometimes used in nest construction. Other types of arthropod also produce silk, most notably various arachnids such as spiders (e.g., spider silk). Silk fibers generated by insects and spiders represent the strongest natural fibers known and rival even synthetic high performance fibers.

Silk has been a highly desired and widely used textile since its first appearance in ancient China (see Elisseeff, "The Silk Roads: Highways of Culture and Commerce," Berghahn Books/UNESCO, New York (2000); see also Vainker, "Chinese Silk: A Cultural History," Rutgers University Press, Piscataway, New Jersey (2004)). Glossy and smooth, silk is favored by not only fashion designers but also tissue engineers because it is mechanically tough but degrades harmlessly inside the body, offering new opportunities as a highly robust and biocompatible material substrate (see Altman et al., Biomaterials, 24: 401 (2003); see also Sashina et al., Russ. J. Appl. Chem., 79: 869 (2006)).

Silk is naturally produced by various species, including, without limitation: *Antheraea mylitta*; *Antheraea pernyi*; *Antheraea yamamai*; *Galleria mellonella*; *Bombyx mori*; *Bombyx mandarina*; *Galleria mellonella*; *Nephila clavipes*; *Nephila senegalensis*; *Gasteracantha mammosa*; *Argiope aurantia*; *Araneus diadematus*; *Latrodectus geometricus*; *Araneus bicentenarius*; *Tetragnatha versicolor*; *Araneus ventricosus*; *Dolomedes tenebrosus*; *Euagrus chisoseus*; *Plectreurys tristis*; *Argiope trifasciata*; and *Nephila madagascariensis*.

As is known in the art, silks are modular in design, with large internal repeats flanked by shorter (~100 amino acid) terminal domains (N and C termini). Naturally-occurring silks have high molecular weight (200 to 350 kDa or higher) with transcripts of 10,000 base pairs and higher and >3000 amino acids (reviewed in Omenatto and Kaplan (2010) Science 329: 528-531). The larger modular domains are interrupted with relatively short spacers with hydrophobic charge groups in the case of silkworm silk. N- and C-termini are involved in the assembly and processing of silks, including pH control of assembly. The N- and C-termini are highly conserved, in spite of their relatively small size compared with the internal modules.

In general, silk fibroin for use in accordance with the present invention may be produced by any such organism, or may be prepared through an artificial process, for example, involving genetic engineering of cells or organisms to produce a silk protein and/or chemical synthesis. In some embodiments of the present invention, silk fibroin is produced by the silkworm, *Bombyx mori*. Fibroin is a type of structural protein produced by certain spider and insect species that produce silk. Cocoon silk produced by the silkworm, *Bombyx mori*, is of particular interest because it offers low-cost, bulk-scale production suitable for a number of commercial applications, such as textile.

Silkworm cocoon silk contains two structural proteins, the fibroin heavy chain (~350 kDa) and the fibroin light chain (~25 kDa), which are associated with a family of nonstructural proteins termed sericin, which glue the fibroin brings together in forming the cocoon. The heavy and light chains of fibroin are linked by a disulfide bond at the C-terminus of the two subunits (see Takei, F., Kikuchi, Y., Kikuchi, A., Mizuno, S. and Shimura, K. (1987) 105 J. Cell Biol., 175-180; see also Tanaka, K., Mori, K. and Mizuno, S. 114 J. Biochem. (Tokyo), 1-4 (1993); Tanaka, K., Kajiyama, N., Ishikura, K., Waga, S., Kikuchi, A., Ohtomo, K., Takagi, T. and Mizuno, S., 1432 Biochim. Biophys. Acta., 92-103 (1999); Y Kikuchi, K Mori, S Suzuki, K Yamaguchi and S Mizuno, "Structure of the *Bombyx mori* fibroin light-chainencoding gene: upstream sequence elements common to the light and heavy chain," 110 Gene, 151-158 (1992)). The sericins are a high molecular weight, soluble glycoprotein constituent of silk which gives the stickiness to the material. These glycoproteins are hydrophilic and can be easily removed from cocoons by boiling in water.

As used herein, the term "silk fibroin" refers to silk fibroin protein, whether produced by silkworm, spider, or other insect, or otherwise generated (Lucas et al., 13 Adv. Protein Chem., 107-242 (1958)). In some embodiments, silk fibroin is obtained from a solution containing a dissolved silkworm silk or spider silk. For example, in some embodiments, silkworm silk fibroins are obtained from the cocoon of *Bombyx mori*. In some embodiments, spider silk fibroins are obtained, for example, from *Nephila clavipes*. In some embodiments, silk fibroins suitable for use in the invention are obtained from a solution containing a genetically engineered silk harvested from bacteria, yeast, mammalian cells, transgenic animals or transgenic plants. See, e.g., WO 97/08315 and U.S. Pat. No. 5,245,012, each of which is incorporated herein as reference in its entirety.

In some embodiments, a silk solution is used to fabricate compositions of the present invention contain fibroin proteins, essentially free of sericins. In some embodiments, silk solutions used to fabricate various compositions of the present invention contain the heavy chain of fibroin, but are essentially free of other proteins. In other embodiments, silk solutions used to fabricate various compositions of the present invention contain both the heavy and light chains of fibroin, but are essentially free of other proteins. In certain embodiments, silk solutions used to fabricate various compositions of the present invention comprise both a heavy and a light chain of silk fibroin; in some such embodiments, the heavy chain and the light chain of silk fibroin are linked via at least one disulfide bond. In some embodiments where the heavy and light chains of fibroin are present, they are linked via one, two, three or more disulfide bonds. Although different species of silk-producing organisms, and different types of silk, have different amino acid compositions, various fibroin proteins share certain structural features. A general trend in silk fibroin structure is a sequence of amino acids that is characterized by usually alternating glycine and alanine, or alanine alone. Such configuration allows fibroin molecules to self-assemble into a beta-sheet conformation. These "Alanine-rich" hydrophobic blocks are typically separated by segments of amino acids with bulky side-groups (e.g., hydrophilic spacers).

Silk fibroin materials explicitly exemplified herein were typically prepared from material spun by silkworm, *Bombyx mori*. Typically, cocoons are boiled in an aqueous solution of 0.02 M $Na_2CO_3$, then rinsed thoroughly with water to extract the glue-like sericin proteins (this is also referred to as "degumming" silk). Extracted silk is then dissolved in a solvent, for example, LiBr (such as 9.3 M) solution at room temperature. A resulting silk fibroin solution can then be further processed for a variety of applications as described elsewhere herein.

In some embodiments, polymers of silk fibroin fragments can be derived by degumming silk cocoons at or close to (e.g., within 5% around) an atmospheric boiling temperature for at least about: 1 minute of boiling, 2 minutes of boiling, 3 minutes of boiling, 4 minutes of boiling, 5 minutes of boiling, 6 minutes of boiling, 7 minutes of boiling, 8 minutes of boiling, 9 minutes of boiling, 10 minutes of boiling, 11 minutes of boiling, 12 minutes of boiling, 13 minutes of boiling, 14 minutes of boiling, 15 minutes of boiling, 16 minutes of boiling, 17 minutes of boiling, 18 minutes of boiling, 19 minutes of boiling, 20 minutes of boiling, 25 minutes of boiling, 30 minutes of boiling, 35 minutes of boiling, 40 minutes of boiling, 45 minutes of boiling, 50 minutes of boiling, 55 minutes of boiling, 60 minutes or longer, including, e.g., at least 70 minutes, at least 80 minutes, at least 90 minutes, at least 100 minutes, at least 110 minutes, at least about 120 minutes or longer. As used herein, the term "atmospheric boiling temperature" refers to a temperature at which a liquid boils under atmospheric pressure.

As used herein, the phrase "silk fibroin fragments" refers to peptide chains or polypeptides having an amino acid sequence corresponding to fragments derived from silk fibroin protein or variants thereof. In the context of the present disclosure, silk fibroin fragments generally refer to silk fibroin peptide chains or polypeptides that are smaller than the naturally occurring full length silk fibroin counterpart, such that one or more of the silk fibroin fragments within a population or composition are less than 300 kDa. The provided silk fibroin fragments may be degummed under a specific condition (e.g., degumming time and atmospheric boiling temperature or a temperature ranging from 90° C. to 110° C.) to produce silk fibroin fragments having a desired molecular weight. In some embodiments, a silk solution may be produced having silk fibroin with a molecular weight that ranges from 3.5 kDa to 300 kDa, from 50 kDa to 120 kDa, or from 120 kDa to 300 kDa. In some embodiments, the molecular weight is at least 3.5 kDa, or at least 5 kDa, or at least 10 kDa, or at least 20 kDa, or at least 30 kDa, or at least 40 kDa, or at least 50 kDa, or at least 60 kDa, or at least 70 kDa, or at least 80 kDa, or at least 90 kDa, to less than 100 kDa, or less than 110 kDa, or less than 120 kDa, or less than 130 kDa, or less than 140 kDa, or less than 150 kDa, or less than 200 kDa, or less than 250 kDa, or less than 300 kDa.

As used herein, "saccharide-substituted silk fibroin" refers to silk fibroin, or fragments thereof, having an amino acid (e.g., serine, threonine, aspartic acid, glutamic acid, and/or tyrosine) covalently coupled to the saccharide. Depending on the amino acid, the saccharide may be directly covalently coupled to the amino acid, or a linker moiety (e.g., diazonium compound, carboxyalkyl compound) may couple the amino acid to the saccharide. The term "linker residue" is used interchangeably with the term "linking agent" as used herein. Referring to FIG. 1, a schematic illustration is provided to show various methods of producing a saccharide-substituted silk fibroin in accordance with various aspects of the present disclosure.

In some embodiments, the saccharide-substituted silk fibroin is produced by contacting a serine or threonine residue of the silk fibroin solution with a carboxyalkyl halogen compound to create a carboxylated serine or threonine residue via nucleophilic substitution. The reaction may occur under basic conditions, for example, at a pH of about 13.5. As used herein, "alkyl" as refers to a straight-chain or branched alkyl radical in all of its isomeric forms, such as a straight or branched group of 1-12, 1-10, or 1-6 carbon atoms, referred to herein as $C_1$-$C_{12}$ alkyl, $C_1$-$C_{10}$-alkyl, and $C_1$-$C_6$-alkyl, respectively. The term "carboxy" as used herein refers to the radical —COOH or its corresponding salts, e.g. —COONa, etc. The term halogen refers to any of the elements fluorine, chlorine, bromine, and iodine. In some non-limiting example, the carboxyalkyl halogen is chloroacetic acid.

The method further includes contacting the carboxylated serine or threonine residue with at least one saccharide in the presence of 1-ethyl-3-(-3-dimethylaminopropyl) carbodiimide hydrochloride (EDC) and N-hydroxysuccinimide (NHS) to create a saccharide-substituted silk fibroin, where a carbonyl residue in the carboxylated serine or threonine residue is covalently coupled to the at least one saccharide. The carbonyl residue may become covalently bonded to an amine residue of the saccharide. The term "carbonyl" as used herein refers to the radical —C(O)—. In some embodiments, the silk fibroin solution is an aqueous silk fibroin solution. In some embodiments, the aqueous silk fibroin solution additional comprises a buffer and the solution is maintained at a pH of about 6.0. As shown in FIG. 1, in addition to coupling the saccharide to the serine of the silk fibroin, the EDC and NHS conditions may simultaneously couple a saccharide to aspartic acid and glutamic acid in the silk fibroin. For example, a carbonyl residue in the aspartic acid and glutamic acid become covalently coupled to the at least one saccharide.

In some embodiments, the carboxylic acids of aspartic acid and glutamic acid are first protected using a carboxylic acid protecting group (e.g., methyl ester, benzyl esters, tert-butyl esters, etc.) prior to EDC and NHS conditions. In this way, the serine residue of the saccharide-substituted may be selectively coupled to the saccharide without side reactions with aspartic acid and glutamic acid. The protecting group may be removed following EDC and NHS conditions, using known methods, such as acid removal, base removal, hydrogenolysis removal. In this reaction pathway, serine and threonine may be selectively substituted with a saccharide. In some embodiments, serine, threonine, aspartic acid, and glutamic acid are selectively substituted with a saccharide using this pathway. In some embodiments, tyrosine remains unsubstituted. As used herein, "unsubstituted" refers to portions of silk fibroin, or fragments thereof, that have not been conjugated with a saccharide. Unsubstituted silk fibroin may still be modified in other ways, substituted with other moieties, or subject to other chemical processes to produce the provided compositions herein.

In some embodiments, the present disclosure provides a method for creating a saccharide-substituted silk fibroin that comprises contacting a silk fibroin solution having aspartic acid and glutamic acid moieties with at least one saccharide in the presence of EDC and NHS. As shown in FIG. 1, under these reaction conditions, a carbonyl residue in the aspartic acid and glutamic acid become covalently coupled to the at least one saccharide. In some embodiments, the carbonyl residue becomes covalently bonded to an amine of the saccharide. In this reaction pathway, aspartic acid and glutamic acid moieties of the silk fibroin may be selectively substituted with a saccharide, while serine, threonine, and tyrosine moieties may remain unsubstituted.

In some embodiments, the present disclosure provides a method for creating a saccharide-substituted silk fibroin comprising the steps of contacting a tyrosine residue of silk fibroin with a diazonium salt. Suitable diazonium salts useful for the methods and compositions described herein, are known to those of skill in the art. A diazonium salt comprises a group of organic compounds with a structure of R—N$_2^+$X$^-$, wherein R can be any organic residue (e.g., alkyl or aryl) and X is an inorganic or organic anion (e.g., halogen). A diazonium salt can be formed by the treatment of aromatic amines (e.g., aniline) with sodium nitrite in the presence of a mineral acid and methods for synthesizing diazonium salts are known to those of skill in the art. See for example WO 2006/014549, WO 2004/108633 and WO 2001/025341, which are incorporated herein by reference. The methods for synthesizing diazonium salts and the chemistries involved in diazonium coupling are well within the ability of one skilled in the art for use with the methods described herein. Diazonium salts for use herein comprise at least one chemical residue, however it is also contemplated that a diazonium salt comprises multiple chemical moieties. In some embodiments, the provided diazonium salts are functionalized with a carboxy or carboxyaryl residue, such as amino benzoic acid diazonium salt. As shown in FIG. 1, the diazonium compound may become covalently bonded to the aromatic ring of tyrosine. In some embodiments, the method further includes contacting the carboxy residue of the diazonium salt with at least one saccharide in the presence of EDC and NHS to create a saccharide-substituted silk fibroin.

In some embodiments, the provided methods may be used in combination to selectively couple a saccharide to a serine, a threonine, a aspartic acid, a glutamic acid, and a tyrosine in the silk fibroin.

In some embodiments, the provided silk fibroin solutions may be processed into a hydrogel, a sponge (i.e., a foam), a film, non-woven mats, and a combination thereof. Silk fibroin-based hydrogels can be prepared from the silk fibroin solutions via many methods including, but not limited to, sonication, pH, vortexing, electric fields, polyols, ion (e.g., calcium) induced sol-gel transition, surfactants, and enzymatic reactions. Sponges may be produced from silk fibroin solutions via many methods including, but not limited to, porogen leaching, gas foaming, and lyophilization. Films may be produced from silk fibroin solutions via many methods, such as, drop casting in a mold and allowing to dry until a dried film is formed. Non-woven silk fibroin mats may be produced from silk fibroin solutions via many methods including, but not limited to, electro spinning.

In some embodiments, the properties of provided compositions may be modulated by controlling a concentration of the silk fibroin solution. In some embodiments, a weight percentage of silk fibroin (including silk fibroin, saccharide-substituted silk fibroin, or combinations thereof) can be present in a solution at any concentration suited to a particular application. In some embodiments, an aqueous silk fibroin solution (or a provided composition, for example, a provided hydrogel, sponge, film, or non-woven mat) can have silk fibroin (including silk fibroin, saccharide-substituted silk fibroin, or combinations thereof) at a concentration of about 0.1 wt % to about 95 wt %, 0.1 wt % to about 75 wt %, or 0.1 wt % to about 50 wt %.

In some embodiments, an aqueous silk fibroin solution (or a provided composition, for example, a provided hydrogel, sponge, film, or non-woven mat) can have silk fibroin (including silk fibroin, saccharide-substituted silk fibroin, or combinations thereof) at a concentration of about 0.1 wt % to about 10 wt %, about 0.1 wt % to about 5 wt %, about 0.1 wt % to about 2 wt %, or about 0.1 wt % to about 1 wt %. In some embodiments, a silk fibroin solution (or a provided composition, for example, a provided hydrogel, sponge, film, or non-woven mat) can have silk fibroin (including silk fibroin, saccharide-substituted silk fibroin, or combinations thereof) at a concentration of about 10 wt % to about 50 wt %, about 20 wt % to about 50 wt %, about 25 wt % to about 50 wt %, or about 30 wt % to about 50 wt %.

In some embodiments, a weight percent of silk (including silk fibroin, saccharide-substituted silk fibroin, or combinations thereof) in solution (or a provided composition, for example, a provided hydrogel, sponge, film, or non-woven mat) is about less than 1 wt %, is about less than 1.5 wt %, is about less than 2 wt %, is about less than 2.5 wt %, is about less than 3 wt %, is about less than 3.5 wt %, is about less than 4 wt %, is about less than 4.5 wt %, is about less than 5 wt %, is about less than 5.5 wt %, is about less than 6 wt %, is about less than 6.5 wt %, is about less than 7 wt %, is about less than 7.5 wt %, is about less than 8 wt %, is about less than 8.5 wt %, is about less than 9 wt %, is about less than 9.5 wt %, is about less than 10 wt %, is about less than 11 wt %, is about less than 12 wt %, is about less than 13 wt %, is about less than 14 wt %, is about less than 15 wt %, is about less than 16 wt %, is about less than 17 wt %, is about less than 18 wt %, is about less than 19 wt %, is about less than 20 wt %, is about less than 25 wt %, or is about less than 30 wt %. In some embodiments, a weight percent of silk (including silk fibroin, saccharide-substituted silk fibroin, or combinations thereof) in solution (or a provided composition, for example, a provided hydrogel, sponge, film, or non-woven mat) is at least 1 wt %, is at least 1.5 wt %, is at least 2 wt %, is at least 2.5 wt %, is at least 3 wt %, is at least 3.5 wt %, is at least 4 wt %, is at least 4.5 wt %, is at least 5 wt %, is at least 5.5 wt %, is at least 6 wt %, is at least 6.5 wt %, is at least 7 wt %, is at least 7.5 wt %, is at least 8 wt %, is at least 8.5 wt %, is at least 9 wt %, is at least 9.5 wt %, is at least 10 wt %, is at least 11 wt %, is at least 12 wt %, is at least 13 wt %, is at least 14 wt %, is at least 15 wt %, is at least 16 wt %, is at least 17 wt %, is at least 18 wt %, is at least 19 wt %, is at least 20 wt %, is at least 25 wt %, or is at least 30 wt %.

In some embodiments, the properties of the provided compositions may be modulated by controlling a concentration and type of saccharide-substituted silk fibroin. In some embodiments, the provided compositions may be modulated by controlling the total amount of hydroxyl moieties from serine and/or threonine that are coupled to at least one saccharide. In some embodiments, the total amount of serine and threonine residues that are coupled to the saccharide (e.g., via the hydroxyl moiety), or the total amount of unsubstituted serine and threonine, ranges from 0.1 mole percent ("mol %") to 12.1 mol %, based on the total number of moles in the saccharide-substituted silk fibroin. In some embodiments, the amount of serine and threonine residues that are covalently coupled to at least one saccharide, or the total amount of unsubstituted serine and threonine, in the provided compositions is at least 0.1 mol %, or at least 0.5 mol %, or at least 1 mol %, or at least 2 mol %, or at least 3 mol %, or at least 4 mol %, or at least 5 mol %, to less than 6 mol %, or less than 7 mol %, or less than 8 mol %, or less than 9 mol %, or less than 10 mol %, or less than 11 mol %, or less than 12.1 mol %, based on the total amount of moles in the saccharide-substituted silk fibroin. In some embodiments, the provided compositions comprise unsubstituted serine and threonine.

In some embodiments, the provided compositions may be modulated by controlling the total amount of carbonyl moieties from aspartic acid and/or glutamic acid that are covalently coupled to the at least one saccharide in the saccharide-substituted silk fibroin. In some embodiments, the total amount of aspartic acid and/or glutamic acid residues that are covalently coupled to the at least one saccharide (e.g., via carbonyl moieties in the aspartic acid and/or glutamic acid), or the total amount of unsubstituted aspartic acid and/or glutamic acid, ranges from 0.01 mol % to 1.1 mol %, based on the total amount of moles in the saccharide-substituted silk fibroin. In some embodiments, the total amount of aspartic acid and/or glutamic acid residues covalently coupled to at least one saccharide is at least 0.01 mol %, or at least 0.1 mol %, or at least 0.2 mol %, or at least 0.3 mol %, or at least 0.4 mol %, or at least 0.5 mol % to less than 0.6 mol %, or less than 0.7 mol %, or less than 0.8 mol %, or less than 0.9 mol %, or less than 1.1 mol %, based on the total amount of moles in the saccharide-substituted silk fibroin. In some embodiments, the provided compositions comprise unsubstituted aspartic acid and glutamic acid.

In some embodiments, the provided compositions may be modulated by controlling the total amount of tyrosine residues covalently coupled to the at least one saccharide. In some embodiments, the total amount of tyrosine residues coupled to the at least one saccharide, or the total amount of unsubstituted tyrosine residues, ranges from 0.01 mol % to 5.3 mol %. In some embodiments, the total amount of tyrosine residues coupled to the at least one saccharide is at least 0.01 mol %, or at least 0.1 mol %, or at least 0.5 mol %, or at least 1 mol %, or at least 2 mol %, or at least 3 mol % to less than 4 mol %, or less than 5.3 mol %. In some embodiments, the provided compositions comprise unsubstituted tyrosine residues.

In some embodiments, the provided compositions may be modulated by controlling the total amount of saccharide in the provided saccharide-substituted silk fibroin compositions. In some embodiments, the saccharide is present in the saccharide-substituted silk fibroin composition in an amount from 0.01 to 0.18 mM, from 0.01 to 0.07, or from 0.01 to 0.03. In some embodiments, the total amount of saccharide is at least 0.01 mM, or at least 0.02 mM, or at least 0.03 mM, or at least 0.04 mM, or at least 0.05 mM, or at least 0.06 mM, or at least 0.07 mM, or at least 0.08 mM to less than 0.09 mM, or less than 0.1 mM, or less than 0.11 mM, or less than 0.12 mM, or less than 0.13 mM, or less than 0.14 mM, or less than 0.15 mM, or less than 0.16 mM, or less than 0.17 mM.

In some embodiments, the degree of substitution is controlled by selecting a desired amount of starting reagents (e.g., saccharide, linking agent, EDC, NHS) in relation to the number of amino acids (e.g., serine, threonine, glutamic acid, aspartic acid, tyrosine) on the silk fibroin, or fragment thereof.

In some embodiments, the provided compositions may be selectively modified using the provided methods to have a desired water contact angle (e.g., a desired hydrophobicity or hydrophilicity). In some embodiments, the water contact angle ranges from 35 to 51 degrees, from 35 to 40 degrees, from 39 to 50 degrees, or from 42 to 51 degrees. In some embodiments, the water contact angle is at least 35 degrees, or at least 40 degrees, or at least 45 degrees, or at least 50 degrees, or at least 55 degrees, or at least 60 degrees. In some embodiments, the water contact angle is less than 60 degrees, or less than 55 degrees, or less than 50 degrees, or less than 45 degrees, or less than 40 degrees. In some embodiments the provided compositions are treated with an alcohol (e.g., methanol), a β-sheet inducing agent or treatment to increase the water contact angle.

In some embodiments, the provided compositions may be modulated to have a surface that resists cell attachment, cell growth, and/or has anti-adhesive properties with respect to cells. In some embodiments, the anti-adhesive properties are selectively modulated by selecting a saccharide. Suitable saccharides that impart anti-adhesive properties include, but are not limited to, monosaccharides, disaccharides, such as glucosamine (GlcN), mannose and combinations or derivaties thereof (e.g., mannosides). In some embodiments, suitable saccharides include, but are not limited to, oligosaccharides and polysaccharides, such as heparin, dextran, cellulose, alginate and a combination thereof.

In some embodiments, the bioactivity and anti-adhesive properties of the provided compositions are tunable. The bioactivity and anti-adhesive properties of the provided compositions may be is measured using a fluorescent dye reduction percentage test. In some embodiments, a surface of the provided compositions is characterized as having a dye reduction percentage of less than 1%, or less than 0.5%, or less than 0.4%, or less than 0.3%, or less than 0.2%, or less than 0.1% after a duration (24 hours to 8 days) following positioning cells on the surface at a cell density of at least 8000 cells/cm$^2$ in a growth medium.

In some embodiments, an example test method for dye reduction percentage may include depositing a composition provided herein on the substrate, and seeding cells on a surface of the provided composition at a cell density of approximately 8000 cells/cm$^2$. Exemplary cells for the test include, but are not limited to, mouse fibroblast cells (L929). The cells may then be submerged in a volume of growth medium, and allowed to spread over the surface of the provided composition for a duration (e.g., 24 hours to 8 days). Suitable growth mediums include, but are not limited to, Dulbecco's Modified Eagle Medium supplemented with or without 10% fetal bovine serum, 1% Penicillin-Streptomycin. Suitable volumes of growth medium range from 0.5 mL to 5 mL (e.g., at least 0.5 mL, at least 1 mL, at least 2 mL, to less than 3 mL, or less than 4 mL, or less than 5 mL). Metabolic activity of the cells may be determined at the specified duration using a metabolic activity assay, such as alamarBlue viability assay (Invitrogen, Carlsbad, CA). The dye reduction for surface metabolic activity is a measure of the decrease in percentage of dye present at the specified duration after normalization to initial measurements.

The present invention has been described in terms of one or more preferred embodiments, and it should be appreciated that many equivalents, alternatives, variations, and modifications, aside from those expressly stated, are possible and within the scope of the invention.

EXAMPLES

Materials and Methods

All materials and commercial reagents were used as purchased. All solvents were used as supplied (analytical or HPLC grade) without further purification.

Preparation of AQUEOUS SILK SOLUTION

Silk fibroin (SF) solutions were prepared using our previously reported protocol.[93] Briefly, 5 grams of *B. mori* silkworm cocoons were cut into small pieces and extracted in 2 L of 0.02 M Na$_2$CO$_3$ solution (Sigma-Aldrich, St. Louis, MO) in a glass beaker for 30 and 120 minutes separately to remove the sericin protein coating. Degummed fibers were collected and rinsed with deionized water (DI) in a 4 L bucket three times for 20 minutes, followed by air-drying in a fume hood overnight. The degummed fibers were solubilized in 9.3 M LiBr (Sigma-Aldrich, St. Louis, MO), the following day, in a pre-heated oven at 60° C. for 4 h. After 4 h, a clear light brown color SF solution was obtained which was then dialyzed against 4 L of DI water with six water changes after 1, 2, 4, 24, 36, and 48 h. The dialysis was performed with a dialysis tube (3,500 MWCO, Thermo Scientific, Rockford, IL). After 48 h, centrifugation of the dialyzed silk solution was performed twice (9,000 RPM, 20 min, 4° C.) to remove insoluble white/brown aggregates. The concentration of the silk solution was determined by drying a known mass of the silk solution in a weighing boat in an oven at 60° C. overnight and assessing the mass of the remaining solid film.

Synthesis of SF(S)—COOH (Step 1, Pathway 1)

The serine residues of silk fibroin (157 and 79 kDa MW SF) are selectively carboxylated by nucleophilic substitution reaction in alkaline condition, in presence of chloroacetic acid (Sigma-Aldrich, St. Louis, MO) at pH 13.3-13.5. Briefly, 0.6 wt % of the silk solution was added to 1 M chloroacetic acid at pH 13.3-13.5. The pH of the 1 M chloroacetic acid was adjusted by adding 10 M sodium hydroxide (NaOH) solution to attain a pH of 13.3-13.5. The mixed solution was stirred for 1 h at RT. After 1 h, sodium phosphate monobasic (NaH$_2$PO4) (Sigma-Aldrich, St. Louis, MO; Lot #015K0024) was added to the reaction at a concentration of 4 mg/mL and stirred until complete dissolution. The pH of the solution was adjusted to 7-7.5 by slow addition of 10 M hydrochloric acid (HCl) (Sigma-Aldrich, St. Louis, MO). The reaction was allowed to be stirred for 30 minutes at RT. After 30 minutes, the carboxylated silk solution was dialyzed against DI water for 72 h with six water changes (1 h, 2 h, 4 h, 24 h, 48 h, and 72 h) to remove impurities. The dialysis was performed with a dialysis tube (3,500 MWCO, Thermo Scientific, Rockford, IL). After dialysis, the carboxy-modified silk solutions were filtered in a sterile cell strainer with 40 μm mesh size (Thermo Scientific, Rockford, IL). After filtration, the solutions were frozen at −80° C. overnight followed by lyophilizing for 72 h. The lyophilized powders were stored at 4° C. until further use.

Synthesis of SF(S)-GlcN (Step 2, Pathway 1)

The serine carboxylated silk solutions (SF(S)—COOH) were conjugated with amines of D-(+)-glucosamine hydrochloride (Sigma-Aldrich, St. Louis, MO) by carbodiimide coupling in presence of N-(3-dimethylaminopropyl)-N'-ethylcarbodiimide hydrochloride (EDC) and N-hydroxy succinimide (NHS) (Sigma-Aldrich, St. Louis, MO). Briefly, 2 wt % of the silk solution was dissolved in 0.1 M MES (2-(N-morpholino) ethanesulfonic acid) buffer at pH 6. D-(+)-glucosamine hydrochloride (10×(10 times molar excess)) was weighed and pre-dissolved in distilled water (Thermo-Fisher Scientific, Waltham, MA) and added to the silk solution. The pH was adjusted to 6 by dropwise addition of freshly prepared 1 M NaOH solutions. EDC (10×) and NHS (10×) were added to the reaction mixture at pH 6. The final MES buffer concentration of the reaction mixture was adjusted to 0.05 M by addition of ultrapure water. The reaction was stirred at RT for 18 h. After the reaction got over, the aggregates were filtered in a sterile cell strainer with 40 μm mesh size (Thermo Scientific, Rockford, IL) before performing dialysis against DI water for 72 h with six water changes (1 h, 2 h, 4 h, 24 h, 48 h, and 72 h). The dialysis was performed with a dialysis tube (3,500 MWCO, Thermo Scientific, Rockford, IL). After dialysis, the solutions were frozen at −80° C. overnight followed by lyophilizing for 72 h. The lyophilized powders were stored at 4° C. until further use.

Synthesis of SF(Y)—COOH (Step 1, Pathway 2)

The tyrosine residues of silk fibroin (157 and 79 kDa MW SF) are selectively carboxylated from reported procedure[62] by diazonium coupling reaction in 100 mM borate buffer at pH 9, in the presence of 4-amino benzoic acid, sodium nitrite (NaNO2) and p-toluene sulfonic acid (Sigma-Aldrich, St. Louis, MO). Briefly, 1.25 mL of 0.2 M 4-amino benzoic acid solution was prepared in acetonitrile (HPLC grade, Fisher Scientific) and cooled in ice. In separate glass vials, 1.6 M aqueous solution of p-toluene sulfonic acid and 0.8 M of NaNO2 was prepared. 625 µL of NaNO2 and p-toluene sulfonic acid was added to 1.25 mL of cold 4-aminobenzoic acid. The mixture turned light brown, vortexed and placed in an ice bath for 15-20 minutes to allow diazonium salt formation. 500 µL, of the freshly prepared diazonium salt solution was added to 2 mL of 10 wt % silk solution in 100 mM borate buffer at pH ~9. After addition of the diazonium salt solution, the color of the reaction mixture turned blood red in color. The final pH of the reaction mixture was adjusted to 9 by addition of freshly prepared 1 M NaOH stock solutions, if needed. The reaction mixture was placed in an ice bath for 20 minutes. After the reaction got over, the reaction solution was diluted with ultrapure water to achieve a final silk solution of 2 wt % and was dialyzed against DI water for 72 h (water changes at 1 h, 2 h, 4 h, 24 h, 48 h, and 72 h). Dialysis was performed with a dialysis tube (3,500 MWCO, Thermo Scientific, Rockford, IL). After dialysis, the solutions were frozen at −80° C. overnight followed by lyophilizing for 72 h. The lyophilized powders were stored at 4° C. until further use.

Synthesis of SF(Y)-GlcN (Step 2, Pathway 2)

The prepared tyrosine carboxylated silk solutions (SF(Y)—COOH) were conjugated with amines of D-(+)-glucosamine hydrochloride (Sigma-Aldrich, St. Louis, MO) by carbodiimide coupling in the presence of EDC and NHS. Briefly, 2 wt % of the silk solution was dissolved in 0.1 M MES buffer at pH 6. D-(+)-glucosamine hydrochloride (10×) was weighed and pre-dissolved in ultrapure water (Thermo-Fisher Scientific, Waltham, MA) and added to the silk solution. The pH was adjusted to 6 by dropwise addition of 1 M NaOH. EDC (10×) and NHS (10×) were added to the reaction mixture at pH 6. Ultrapure water was added to the reaction to maintain the final MES buffer concentration to 0.05 M. The reaction was stirred at RT for 18 h. After the reaction got over, the aggregates were filtered in a sterile cell strainer with 40 µm mesh size (Thermo Scientific, Rockford, IL) before starting dialysis against DI water for 72 h (water changes at 1 h, 2 h, 4 h, 24 h, 48 h, 72 h). The dialysis was performed with a dialysis tube (3,500 MWCO, Thermo Scientific, Rockford, IL). After dialysis, the solutions were frozen at −80° C. overnight followed by lyophilizing for 72 h. The lyophilized powders were stored at 4° C. until further use.

Synthesis of SF(D, E)-GlcN (Pathway 3)

The carboxylic acids of as prepared silk solutions of different MW distribution (157 and 79 kDa) (Asp and Glu residues) were conjugated with amines of D-(+)-glucosamine hydrochloride (Sigma-Aldrich, St. Louis, MO) by carbodiimide coupling in presence of EDC and NHS. Briefly, 2 wt % of the silk solution was dissolved in 0.1 M MES buffer at pH 6. D-(+)-glucosamine hydrochloride (10×) was weighed and pre-dissolved in Ultrapure™ distilled water (Thermo-Fisher Scientific, Waltham, MA) and added to the silk solution. The pH was adjusted to 6 by dropwise addition of 1 M NaOH. EDC (10×) and NHS (10×) were added to the reaction mixture at pH 6. Ultrapure™ distilled water was added to the reaction to maintain the final MES buffer concentration to 0.05 M. The reaction was allowed to stir at RT for 18 h. After 18 h, the reaction mixture was filtered in a sterile cell strainer with 40 µm mesh size (Thermo Scientific, Rockford, IL) to remove any aggregates before starting dialysis against DI water for 72 h (water changes at 1 h, 2 h, 4 h, 24 h, 48 h, and 72 h). The dialysis was performed with a dialysis tube (3,500 MWCO, Thermo Scientific, Rockford, IL). After dialysis, the solutions were frozen at −80° C. overnight followed by lyophilizing for 72 h. The lyophilized powders were stored at 4° C. until further use.

Synthesis of SF(S)-EDA

The carboxylated silk solutions (SF(S)—COOH) of 157 kDa MW SF were conjugated with amines of ethylene diamine (EDA) hydrochloride (Sigma-Aldrich, St. Louis, MO) by carbodiimide coupling in the presence of EDC and NHS (Sigma-Aldrich, St. Louis, MO). Briefly, 2 wt % of the silk solution was dissolved in 0.1 M MES (2-(N-morpholino) ethanesulfonic acid) buffer at pH 6. EDA (10×) was weighed and pre-dissolved in Ultrapure™ distilled water (Thermo-Fisher Scientific, Waltham, MA) and added to the silk solution. The pH was adjusted to 6 by dropwise addition of freshly prepared 1 M sodium hydroxide (NaOH) solution. EDC (10×) and NHS (10×) were added to the reaction mixture at pH 6. The final MES buffer concentration of the reaction mixture was adjusted to 0.05 M by addition of Ultrapure™ distilled water. The reaction was stirred at RT for 18 h. After the reaction got over, the aggregates were filtered in a sterile cell strainer with 40 µm mesh size (Thermo Scientific, Rockford, IL) and dialyzed against DI water for 72 h with six water changes (1 h, 2 h, 4 h, 24 h, 48 h, and 72 h). The dialysis was performed with a dialysis tube (3,500 MWCO, Thermo Scientific, Rockford, IL). After dialysis, the solutions were frozen at −80° C. overnight followed by lyophilizing for 72 h. The lyophilized powders were stored at 4° C. until further use.

Synthesis of SF(S)-Digal

The EDA conjugated silk solutions (SF(S)-EDA) of 157 kDa MW SF were carbodiimide coupled with the carboxylic acids of digalacturonic acid (Sigma-Aldrich, St. Louis, MO) in the presence of EDC and NHS (Sigma-Aldrich, St. Louis, MO). Briefly, 2 wt % of the SF(S)-EDA solution was dissolved in 0.1 M MES buffer at pH 6. Digalacturonic acid (10×) was weighed and pre-dissolved in Ultrapure™ distilled water and added to the SF(S)-EDA solution. The pH was adjusted to 6 by dropwise addition of freshly prepared 1 M NaOH solution. EDC (10×) and NHS (10×) were added to the reaction mixture at pH 6. The final MES buffer concentration of the reaction mixture was adjusted to 0.05 M by addition of Ultrapure™ distilled water. The reaction was stirred at RT for 18 h. After the reaction got over, the reaction solution was filtered in a sterile cell strainer with 40 µm mesh size (Thermo Scientific, Rockford, IL) and dialyzed against DI water for 72 h with six water changes (1 h, 2 h, 4 h, 24 h, 48 h, and 72 h). The dialysis was performed with a dialysis tube (3,500 MWCO, Thermo Scientific, Rockford, IL). After dialysis, the solutions were frozen at −80° C. overnight followed by lyophilizing for 72 h. The lyophilized powders were stored at 4° C. until further use.

Preparation of SF and SF-GlcN Films and Sponges

Films were prepared by reconstituting 3 wt % of the SF-GlcN prepared in different pathways in Ultrapure™ distilled water and drop casting in a polydimethylsiloxane (PDMS) mold and allowed to dry overnight in a fume hood.

The dried films were treated with methanol overnight and then dried at RT in a fume hood.

Sponges were prepared by freezing 8 wt % of the SF-GlcN synthesized in different pathways overnight at −20° C. before lyophilizing them for 72 h. The lyophilized sponges were methanol treated overnight to render water insolubility followed by drying at RT in a fume hood before further analysis. The term "sponge" is used interchangeably with the term "foam" herein.

$^1$H-Nuclear Magnetic Resonance Spectroscopy (NMR)

In order to confirm the structures of final lyophilized SF, SF-GlcN powders and reaction intermediates in different modification pathways, the powders were reconstituted in deuterated water (D$_2$O) with concentration of 10-15 mg/mL and performed with a 500 MHz Bruker NMR spectrometer. The spectra analysis was performed in Top Spin 3.6.1 software.

Water Contact Angle Measurement 3 wt % of unmodified silks, glucosamine modified silks in different pathways were prepared in Ultrapure™ distilled water and were cast onto glass slides and dried overnight in a fume hood. Films were treated with methanol overnight and then dried at RT. Contact angle were measured for both as cast and methanol treated films, using a goniometer with a 10 μL water drop size. Four films of each type were analyzed, and each film was measured in at least one area.

Fourier Transform Infrared (FT-IR) Spectroscopy

Protein secondary structures of as SF-GlcN powders, films and sponges synthesized in different modification routes, were determined using a JASCO FTIR 6200 spectrometer (JASCO, Tokyo, Japan) with a MIRacle attenuated total reflectance (ATR) with germanium crystal. FT-IR measurements were performed by averaging 32 scans with a resolution of 4 cm$^{-1}$ within the wavenumber range of 600 and 4000 cm$^{-1}$. FT-IR spectra of degummed and regenerated SF (157 and 79 kDa MW SF), SF-GlcN films (3 wt %) and sponges (6 wt %) prepared from different modification pathways were measured before and after methanol treatment. Data analysis and percentage β-sheet content were performed and calculated using the Fourier self-deconvolution method using Origin software (Origin 2020, OriginLab, Northampton, MA).

Liquid Chromatography Tandem Mass Spectrometry LC-MS/MS

Glucosamine substitution onto SF (157 and 79 kDa MW SF) were analyzed from the hydrolyzed SF-GlcN as synthesized powders using LC-MS/MS (Agilent 1200 series high performance liquid chromatography (HPLC) instrument and an Agilent 6410 triple-quadruple mass spectrometer, Agilent Technologies, Santa Clara, CA) operated in positive electrospray ionization mode. 1 mL of 4 mg/mL silk-GlcN powders were immersed in 1 mL of hydrochloric acid (HCl, 37%, Sigma-Aldrich, St. Louis, MO) at 60° C. for 8 h in a digital dry heat bath. The hydrolyzed samples were dehydrated at 90° C. overnight using a digital dry heat bath (Model: BSH1002, USA Scientific, Ocala, FL). The solid samples were then reconstituted in 1 mL of 75% (v/v) acetonitrile (LC-MS grade, Fisher Scientific, Waltham, MA) in water (LC-MS grade, Fisher Scientific, Waltham, MA), diluted with 75% (v/v) acetonitrile in water to a concentration of 400 μg/mL, followed by transferring to a 96-well plate (Agilent Technologies, Santa Clara, CA). 20 μL samples were injected into a hydrophobic interaction liquid chromatography (HILIC) column (Zorbax HILIC Plus, 4.6× 100 mm, 3.5 μm, Agilent Technologies, Santa Clara, CA) at 37° C. using a gradient elution method at flow rate of 1 mL/min. The gradient method was as follows: 95:5 acetonitrile (0.1% v/v formic acid, Sigma-Aldrich, Saint Louis, MO) to water (0.1% v/v formic acid) for 1 min, adjusted to 5:95 acetonitrile to water over 5 min, held for 2 min, and then returned to 95:5 acetonitrile to water. Product ions for glucosamine (m/z transitions: 180.1→162.2, 180→84, and 180→72)[66] were identified using a product ion scan, where the typical retention times were ~4.5 min. This information was integrated into a multiple reaction monitoring (MRM) program in the Agilent MassHunter Qualitative Data Analysis software (Agilent Technologies, Santa Clara, CA).

Standard Curve

Glucosamine standard curves were run with 0 to 0.116 mM of D-(+)-glucosamine hydrochloride. To account for the instrument drift and matrix effects, 0.012 mM of D-glucosamine-1-$^{13}$C hydrochloride internal standard (m/z transitions: 181→163, 181→85, and 181.1→73)[66] was added to all unknown silk and glucosamine modified silk samples. Peak areas were measured using Agilent MassHunter Qualitative Data Analysis software. Standard curves were generated by plotting the response ratio versus the amount ratio of the analyte to the internal standard, as follows[94]:

$$\text{Amount Ratio } (AR) = \frac{\text{Analyte } (mM)}{\text{Internal Standard } (mM)} \quad (1)$$

$$\text{Response Ratio } (RR) = \frac{\text{Analyte Area}}{\text{Internal Standard Area}} \quad (2)$$

The concentrations of D-(+)-glucosamine incorporated onto SF chains were derived from the respective standard curves based on the internal standard and analyte peak areas, as follows:

$$\text{Analyte } (mM) = \frac{\text{Internal Standard } (mM) \times (RR-b)}{m} \quad (3)$$

where m and b are the slope and intercept of the standard curve: y=mx+b.

Cell Culture

For cell viability and metabolic activity studies, commercial L929 mouse fibroblast cells (ATCC, Manassas, VA) were cultured in growth media composed of Dulbecco's Modified Eagle Medium (DMEM, Gibco) supplemented with 10% fetal bovine serum and 1% penicillin-streptomycin (Life Technologies, Carlsbad, CA). Cells at passage 7 were seeded at a density of 8,000 cells cm$^{-2}$ on the surface of methanol treated films and sponges prepared in different pathways of different molecular weight distributions. The media was changed every 3 days. Cell viability was examined using LIVE/DEAD Cell Imaging Kit (Invitrogen by Thermo Fisher Scientific) after being cultured for 1 and 8 days. Films and sponges were imaged using a BZ—X700

Fluorescence Microscope (Keyence Corp., Itasca, IL) or TCS SP8 confocal laser scanning microscope (CLSM) (Leica Microsystems, Wetzlar, Germany), respectively. Metabolic activity at days 1 and 8 was determined using alamarBlue assay by incubating cells in 500 µL dye solution (10% v/v in DMEM high glucose colorless (Gibco) solution) for 2 h at 37° C. and 5% $CO_2$. Absorbance was measured at 570 nm (reduced) and 595 nm (oxidized) using a Spectra-Max M2 multi-mode microplate reader (Molecular Devices, Sunnyvale, CA). Dye reduction (%) was calculated as described in the assay guidance manual.

Statistics

ATR-FTIR, LC-MS/MS, were performed on n=3 independent sample replicates at each condition. WCA was performed on n=4 independent sample replicates. All data are expressed as means±standard deviations and used to generate graphical figures. One or two-way analysis of variance (ANOVA) with turkey's post-hoc multiple comparison test, Bonferoni test and unpair t-test were performed using GraphPad prism (GraphPad Software, San Diego, CA) to determine statistical significance (*$p<0.03$, $p<0.01$, *$p<0.001$).

Results

1. Reaction Pathways for Modifying Silk Fibroin with a Monosaccharide

SF, extracted from *Bombyx mori* silkworm, is composed of a heavy and light chain protein which are linked through a single disulfide bond[55] to form approximately a 420 kDa molecular weight protein polymer.[56] The majority of the amino acids in silk fibroin are chemically inert, limiting routes for chemical modifications on silks. The amino acids with side chain functional groups such as serine (Ser, S), threonine (Thr, T)), tyrosine (Tyr, Y), aspartic acid (Asp, D), glutamic acid (Glu, E) and lysine (Lys, K) are targets for modifications and constitute 12.1, 0.9, 5.3, 0.5, 0.6, 0.2 mol % of the heavy chain silk fibroin, respectively.[1]

D-(+)-glucosamine (GlcN) was utilized for the examples provided herein, due to its useful features as: i) a common dietary supplement; 2) an amino sugar and one of the most abundant monosaccharides;[57] iii) a key monomer in structural polysaccharides, such as chitosan, chitin[58]; and iv) an important precursor for the synthesis of many glycosylated proteins and lipids.[59]

Distinct synthetic pathways were employed in order to incorporate GlcN via different covalent conjugation methods and to achieve different degrees of substitution (FIG. 1). Pathway 1 involves multiple steps, first, enriching carboxyl residues of silk fibroin by carboxylation of 'Ser' residues by nucleophilic substitution of chloroacetic acid at high pH (13.3-13.5).[60-61] Step 2 involves carbodiimide coupling[16, 61] of the carboxy rich SF with the amines of GlcN in the presence of EDC and NHS to obtain SF (S)-GlcN conjugates.

Pathway 2 also involves two steps to incorporate GlcN onto SF chains. Step 1 involves carboxylation of 'Tyr' residues by diazonium coupling chemistry[62] by the formation of a diazonium salt with 4-aminobenzoic acid. In step 2, carbodiimide coupling was performed on the carboxy enriched 'Tyr' units with the amines of GlcN to obtain SF(Y)-GlcN. Pathway 3 involves the direct carbodiimide coupling of GlcN with carboxy residues (Asp and Glu residues) already present in native silk fibroin. All three-modification pathways are distinct, as they exploit different reactive sites for GlcN conjugation. Pathways 1, 2, 3 have 737, 332 and 55 theoretical carboxy-residues[1] due to 'Ser, Thr, Asp, Glu', 'Tyr, Asp, Glu' and 'Asp, Glu', respectively, and can achieve a maximum substitution of 14.1, 6.4 and 1.1 mol %, respectively.

Figure 2B:
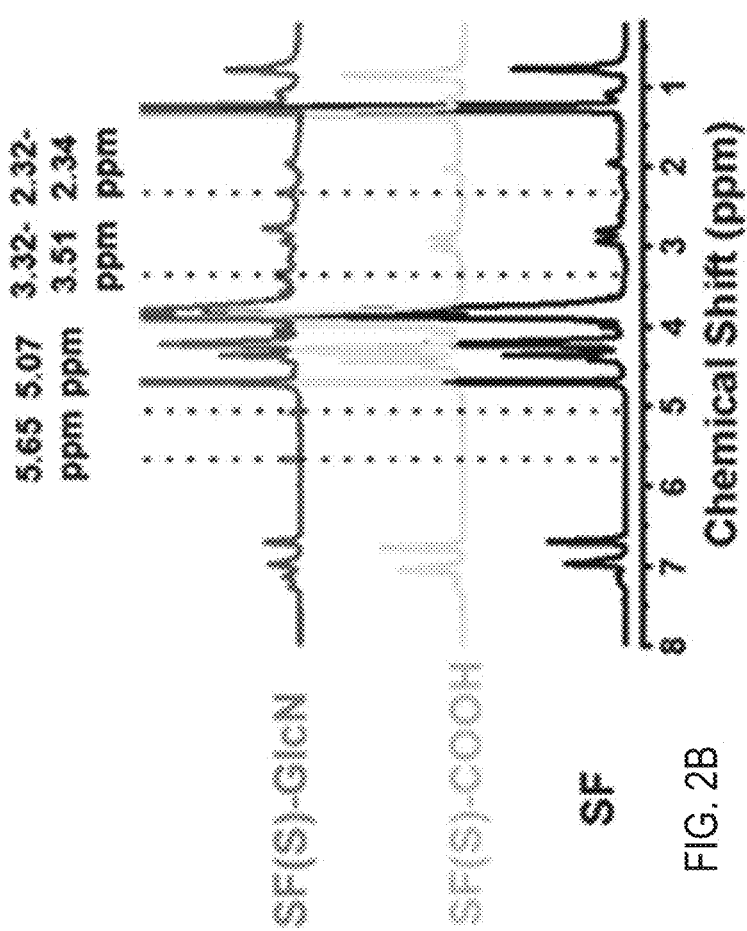
FIG. 2B shows nuclear magnetic resonance (NMR) spectroscopic validation of covalent conjugation of saccharides on silk fibroin with different modification pathways in accordance with embodiments of the present disclosure. 1H-NMR spectroscopy of GlcN functionalized SF (79 kDa MW), the corresponding carboxy intermediates and control (SF) in pathway 1: SF (S)-GlcN, carboxy intermediate SF(S)—COOH, and SF.
Figure 2A:
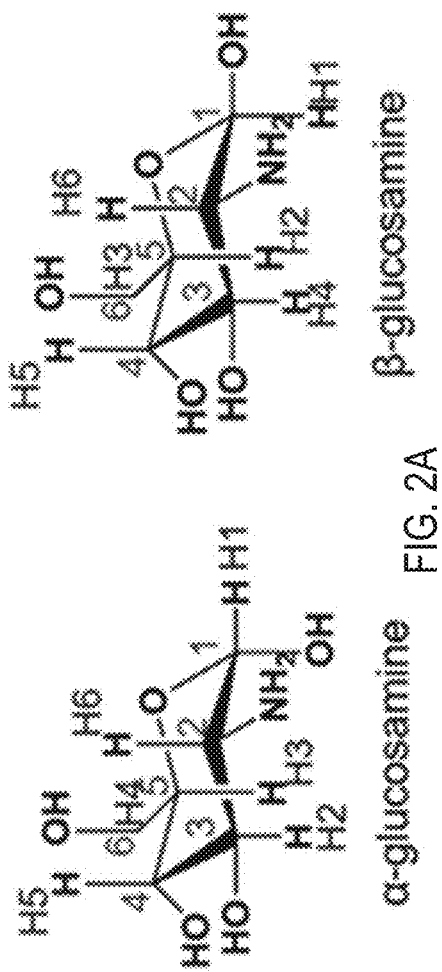
FIG. 2A shows nuclear magnetic resonance (NMR) spectroscopic validation of covalent conjugation of saccharides on silk fibroin with different modification pathways in accordance with embodiments of the present disclosure. Chemical structure of α- and β-glucosamine with protons and carbons labeled for easy interpretation and assignment of peaks and shifts in 1H-NMR spectrum.
Figure 2C:
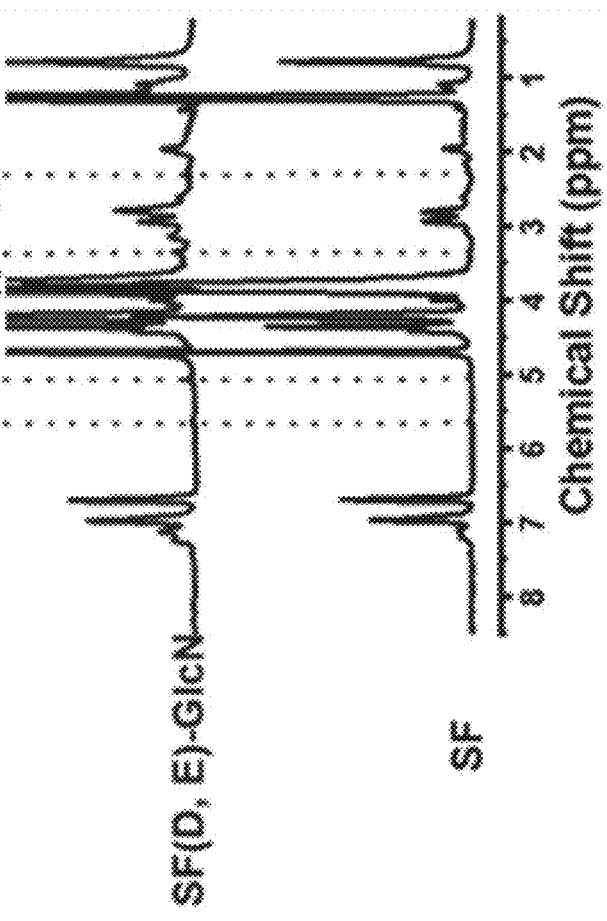
FIG. 2C shows nuclear magnetic resonance (NMR) spectroscopic validation of covalent conjugation of saccharides on silk fibroin with different modification pathways in accordance with embodiments of the present disclosure. 1H-NMR spectroscopy of GlcN functionalized SF (79 kDa MW), the corresponding carboxy intermediates and control (SF) in pathway 2: SF (Y)-GlcN, carboxy intermediate SF(Y)—COOH, and only SF.
Figure 2D:
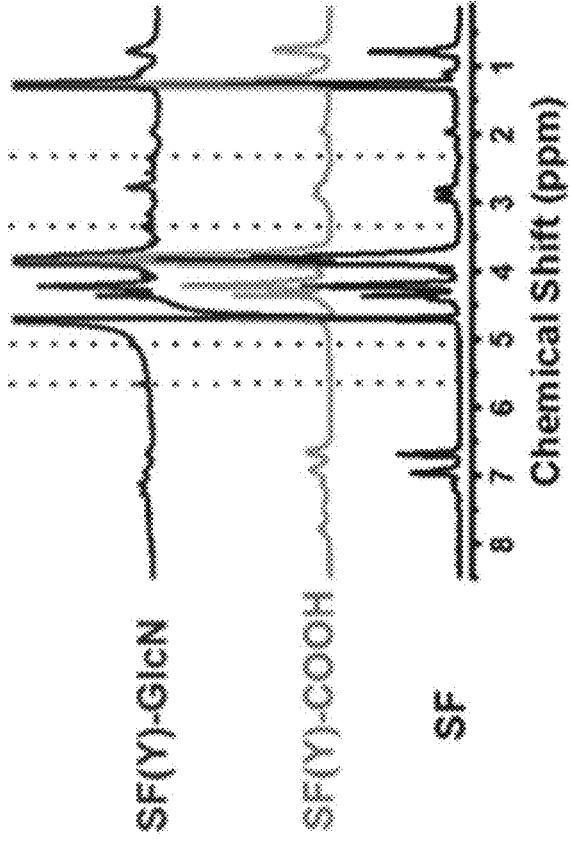
FIG. 2D shows nuclear magnetic resonance (NMR) spectroscopic validation of covalent conjugation of saccharides on silk fibroin with different modification pathways in accordance with embodiments of the present disclosure. 1H-NMR spectroscopy of GlcN functionalized SF (79 kDa MW), the corresponding carboxy intermediates and control (SF) in pathway 3: SF (D, E)-GlcN and only SF. The peaks at 5.65 and 5.07 ppm correspond to anomeric H1α and H1β of GlcN in all pathways. The peaks at 3.32-3.51 and 2.32-2.34 ppm correspond to α and β hydrogens present at C2-C6 positions in GlcN. The NMR spectra are normalized to 1 and plotted using Origin 2020 software.

For synthesis of SF-GlcN constructs with different modification pathways, two different molecular weight (MW) distributions of SF (157 and 79 kDa as peak MW)[63] were used as starting polymers. The longer extraction time results in the lower MW distribution due to chain scission.[63] In pathway 1, carboxylated SF constructs (SF(S)—COOH) with the two different MW distributions were obtained by performing a nucleophilic substitution reaction on the 'Ser' residues in alkaline conditions (pH 13.3-13.5) in the presence of chloroacetic acid.[60] The carboxylated constructs were then coupled with GlcN in the presence of EDC/NHS at pH 6 in 0.05 M MES buffer to obtain SF(S)-GlcN constructs. Both carboxylation and GlcN conjugation steps were monitored by $^1$H-NMR spectroscopy to confirm the carboxylic acid substitution and GlcN conjugation steps (FIG. 2B). In the carboxylation step, the two methylene hydrogens (from chloroacetic acid residues) were expected to have $^1$H-NMR peaks around 4.1-4.3 ppm. However, these peaks could not be observed clearly due to possible overlap with the broad NMR signal at 4.18-4.23 ppm (due to the Ala α, Ser α hydrogens) and 3.79-3.87 ppm (Gly α, Ser β hydrogens) in the silk backbone.[61]

The incorporation of GlcN to SF(S)—COOH by carbodiimide coupling was confirmed by $^1$H-NMR spectroscopy where distinct NMR signature peaks related to GlcN hydrogens were observed in the modified constructs (SF(S)-GlcN). The anomeric hydrogens (H1α and H1β) of GlcN (which undergo mutarotation in aqueous solutions) present in the C1 position, usually have a chemical shift of 5.35 and 4.86 ppm with free glucosamine.[64] However, when covalently conjugated to the carboxy residues of SF, these NMR signature peaks deshielded to 5.65 and 5.07 ppm, respectively, indicating changes in the local chemical environment and chemical conjugation.

In addition to the anomeric hydrogen peaks, GlcN hydrogen peaks were also observed at 3.32-3.51, 2.32-2.34 ppm, which could be due to α and β hydrogens present at the C2-C6 positions in GlcN.[64] To confirm that GlcN was not trapped (noncovalently bound) in the silk polymer chains, a control experiment was performed where serine carboxylated higher MW SF (157 kDa) (SF(S)—COOH) and GlcN were mixed in similar reaction conditions but without EDC and NHS. The reaction mixture was lyophilized before dialysis. $^1$H-NMR showed the proton peaks due to GlcN were observed as in case of free GlcN and without any change in chemical shifts in the spectrum. This result indicated the presence of GlcN in free molecular form and not conjugated to the SF chains.

In pathway 2, carboxylated SF constructs (SF(S)—COOH) with the two different MW distributions were obtained by performing diazonium coupling[62] on the 'Tyr' units in alkaline conditions (pH 9) in the presence of 4-amino benzoic acid in 100 mM borate buffer. The 'Tyr' carboxylated SF constructs (SF(Y)—COOH) were further coupled with GlcN in similar carbodiimide reaction conditions as described in pathway 1. The structural changes due to diazonium and carbodiimide coupling in pathway 2 were monitored using $^1$H-NMR. Diazonium coupling of 'Tyr' units introduced two new broad peaks in the aromatic region at 7.78-7.86, 7.93-7.97 ppm in the case of SF(Y)—COOH starting from 157 kDa MW SF, and 7.33-7.6, 7.77-7.84 ppm in case of 79 kDa SF(Y)—COOH which are due to the azo groups in the diazo-coupled silks.[62] The incorporation of GlcN to SF(Y)—COOH by carbodiimide coupling was confirmed by $^1$H-NMR where distinct NMR signature peaks related to GlcN hydrogens were observed in the modified constructs (SF(Y)-GlcN) as observed for pathway 1.

In pathway 3, the regenerated silk solutions were used directly to conjugate GlcN by carbodiimide coupling utilizing the carboxy groups of Asp and Glu present in native SF to obtain SF (D, E)-GlcN constructs. The addition of GlcN onto silk chains was confirmed using $^1$H-NMR, where distinct GlcN peaks due to the anomeric α and β hydrogens at C1 positions and other protons peaks in the aliphatic region were observed as in pathways 1 and 2. In all three pathways, $^1$H-NMR confirmed the conjugation of GlcN to silk chains for the different MW distributions.

2. Reaction Pathways for Modifying Silk Fibroin with a Disaccharide

The synthetic steps in pathways described above were extended to a disaccharide, digalacturonic acid (Digal). Digal contains two carboxylic acid residues which can be leveraged to conjugate primary amines via carbodiimide coupling onto SF chains. Step 1 involved enriching the carboxyl residues of silk fibroin by carboxylation of 'Ser' residues by nucleophilic substitution of chloroacetic acid at high pH (13.3-13.5) as described above. Step 2 involved conjugation of ethylene diamine with the carboxylic acid residues of SF to enhance the amine content to obtain SF(S)-EDA as reported earlier.[61] In the final step, carbodiimide coupling was performed in the presence of EDC/NHS at pH 6 using the carboxy moieties of the Digal with the amines of the modified SF to obtain Digal modified SF (SF(S)-Digal).

Different versions of the Digal modification steps were characterized by $^1$H-NMR spectroscopy and the chemical shifts interpreted and compared with the chemical shifts of Digal protons[65] in free molecular form. The modification of EDA to SF(S)—COOH was confirmed by the presence of additional proton peaks (in addition to Tyr β protons) due to methylene hydrogens in the aliphatic region. The incorporation of Digal in SF(S)-Digal was confirmed by the presence of signature peaks and changes in chemical shifts of the Digal.

The protons due to Digal in SF(S)-Digal have chemical shifts of 5.20, (5.04, 4.99), 4.48, (4.35, 4.3) ppm (5.22, (4.96, 4.93), 4.52, (4.32, 4.27) in molecular form, respectively) due to H-1α, H-1', H-5, H-1β, respectively. The peaks due to H-4, H-3 and H-2 protons could not be distinguished clearly, likely because of the overlap of broad NMR peaks due to the Alaα/Serα hydrogens (3.87 ppm) of SF. The successful covalent conjugation of GlcN (monosaccharide) and Digal (disaccharide) onto SF chains indicates the versatility and generalizability of our modification protocols that can be applied from simple monosaccharides to increasingly complex sugars (di-, oligosaccharides) across diverse molecular weight distributions of SF. The modification protocols are reproducible, robust, facile and scalable.

3. Quantification of Saccharide Substitution by Mass Spectroscopy

In order to gain insight into the role of the different modification pathways and SF MW distributions on GlcN experimental substitution efficiencies, liquid chromatography tandem mass spectrometry (LC-MS/MS) was performed (FIGS. 3(A-F)). For direct quantitative determination of GlcN substituted onto SF chains, a sensitive and specific LC-MS/MS method was developed based on reported procedures.[66] The possible product ion peaks for GlcN were identified (m/z transitions: 180.1→162.2, 180.1→84 and 180.1→72) and quantified where the typical retention time for GlcN was 4.46 and 4.55 minute substituted in 79 and 157 kDa MW SF, respectively, in all pathways (FIG. 3A, FIG. 3B, FIG. 3C).

Figure 3A:
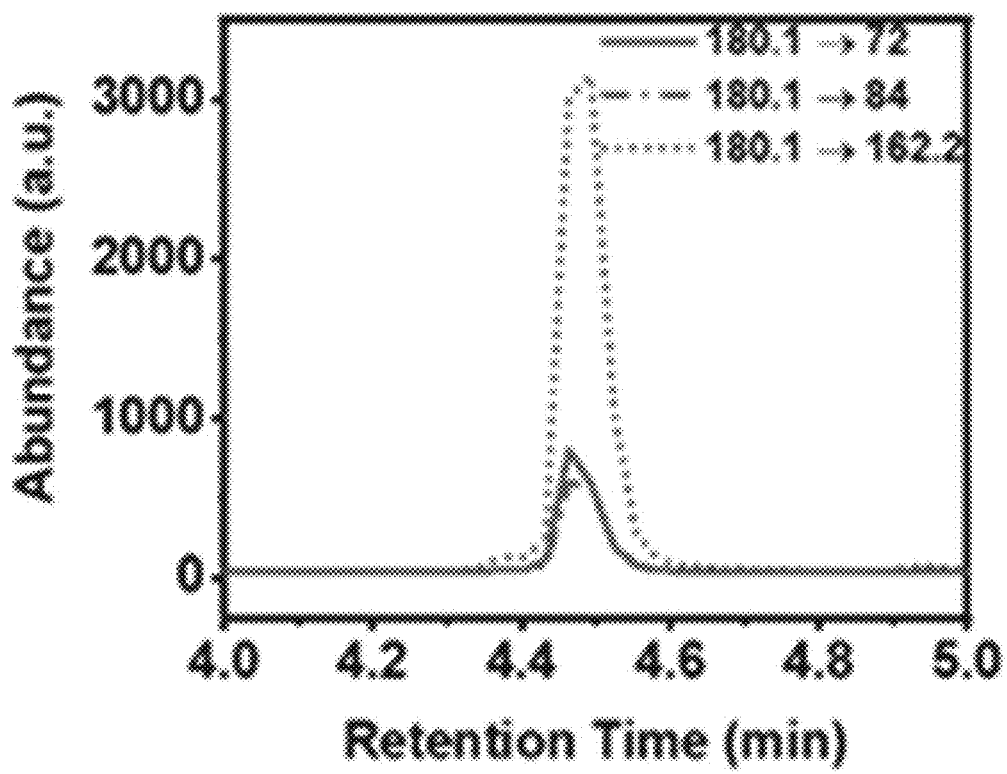
FIG. 3A shows Liquid Chromatography tandem Mass Spectroscopic (LCMS/MS) validation of glucosamine functionalization on silk fibroin (SF) with modification pathway 1 and its pathway-dependent substitution. Representative LC-MS/MS chromatograms obtained from analysis of SF-GlcN conjugates prepared in modification pathway 1 starting from 79 kDa MW SF. Product ions for glucosamine (m/z transitions=180.1→162.2 (dotted line), 180.1→84 (dash-dot-dash line), 180.1→72 (solid line) where typical retention time is 4.46 minutes.
Figure 3B:
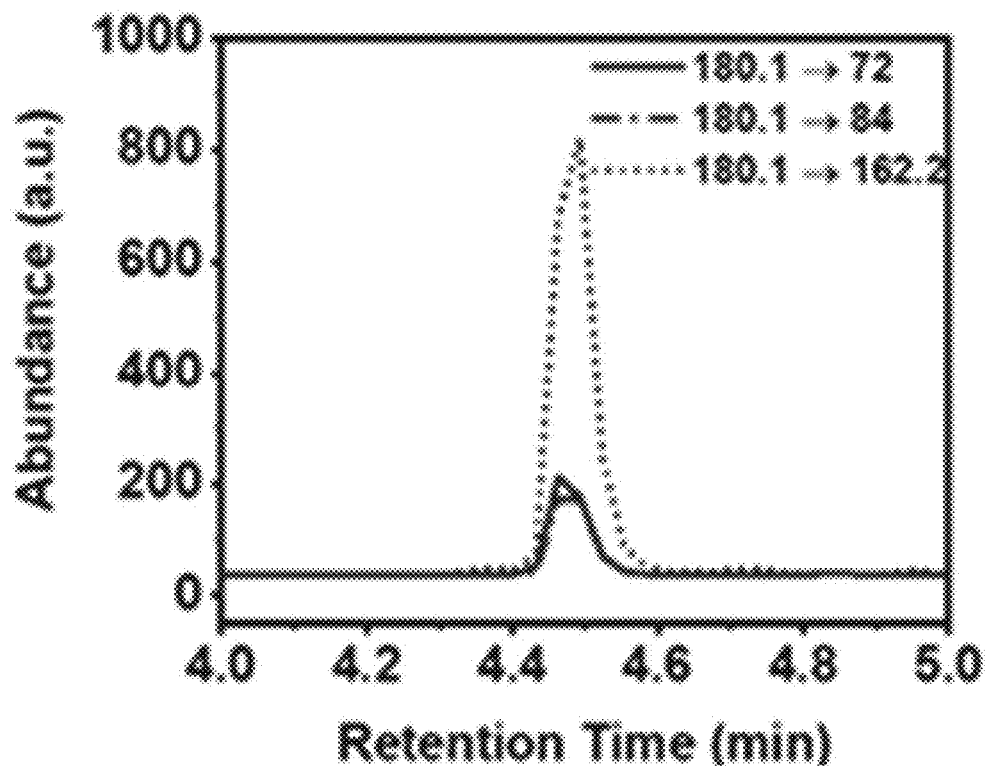
FIG. 3B shows Liquid Chromatography tandem Mass Spectroscopic (LCMS/MS) validation of glucosamine functionalization on silk fibroin (SF) with modification pathway 2 and its pathway-dependent substitution. Representative LC-MS/MS chromatograms obtained from analysis of SF-GlcN conjugates prepared in modification pathways 2 starting from 79 kDa MW SF. Product ions for glucosamine (m/z transitions=180.1→162.2 (dotted line), 180.1→84 (dash-dot-dash line), 180.1→72 (solid line) where typical retention time is 4.46 minutes.
Figure 3C:
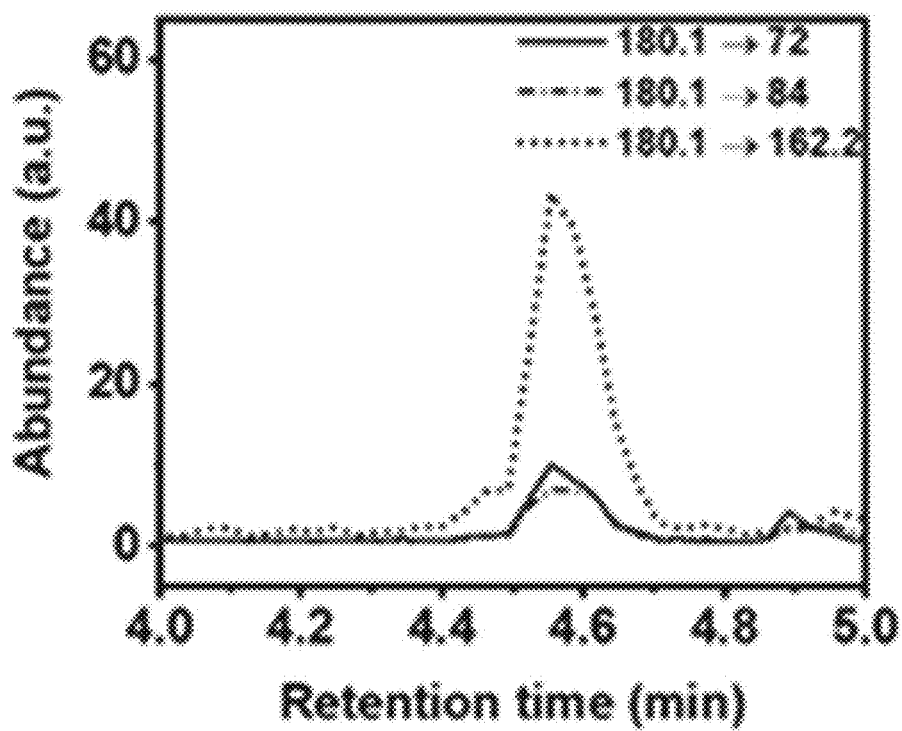
FIG. 3C shows Liquid Chromatography tandem Mass Spectroscopic (LCMS/MS) validation of glucosamine functionalization on silk fibroin (SF) with modification pathway 1 and its pathway-dependent substitution. Representative LC-MS/MS chromatograms obtained from analysis of SF-GlcN conjugates prepared in modification pathway 3 starting from 79 kDa MW SF. Product ions for glucosamine (m/z transitions=180.1→162.2 (dotted line), 180.1→84 (dash-dot-dash line), 180.1→72 (solid line) where typical retention time is 4.46 minutes.
Figure 3D:
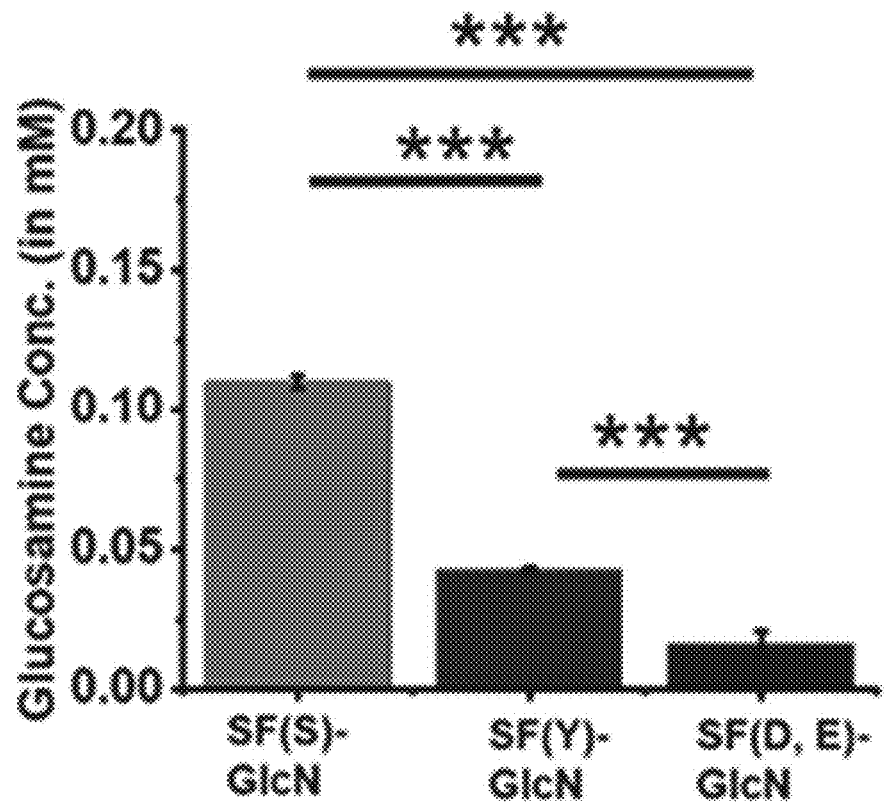
FIG. 3D is a quantification of glucosamine substituted on silk fibroin of 157 kDa molecular weight with different modification pathways; pathway 1: left, pathway 2: middle, pathway 3: right. The order of glucosamine substitution is pathway 1>pathway 2>pathway 3.
Figure 3E:
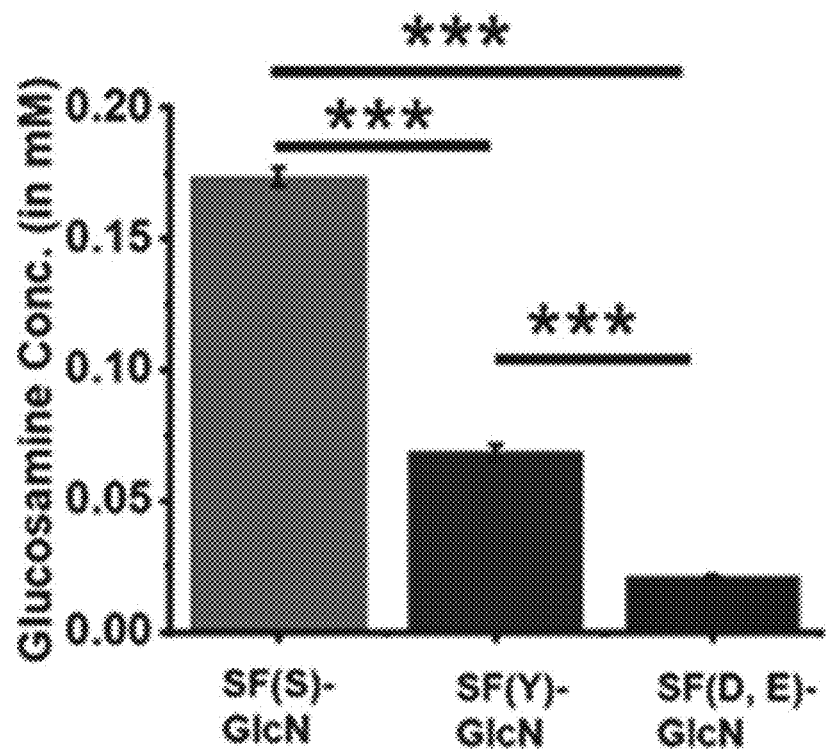
FIG. 3E is a quantification of glucosamine substituted on silk fibroin of 79 kDa with the different modification pathways; pathway 1: left, pathway 2: middle, pathway 3: right. The order of glucosamine substitution is pathway 1>pathway 2>pathway 3.

For quantification of GlcN, a standard curve was obtained by measuring different concentrations of GlcN (0, 0.004, 0.007, 0.014, 0.029, 0.058, and 0.116 mM) at similar experimental condition. For standard curves, $^{13}$C-D-glucosamine (0.012 mM) was used as an internal standard. FIG. 3D and FIG. 3E show the abundance of glucosamine substitution in mM concentration onto SF chains of 157 and 79 kDa MW distributions, respectively, in multiple modification pathways (1, 2 and 3). SF (S)-GlcN (pathway 1), SF(Y)-GlcN (pathway 2), SF(D, E)-GlcN (pathway 3) substitute 0.17±0.003, 0.07±0.003, 0.02±0.0004 mM for lower MW SF (79 kDa SF) and 0.11±0.002, 0.04±0.0006, 0.016±0.004 mM for higher MW SF (157 kDa SF), respectively.

The results demonstrate that: 1) SF with a lower MW distribution results in a higher degree of substitution with GlcN; 2) different modification pathways substitute different amounts of GlcN onto the SF chains, with the order of GlcN substitution Pathway 1>Pathway 2>Pathway 3 in both MWs of the SF chains. In lower MW SF, the carbodiimide conjugation occurs in a comparatively more homogeneous environment than with the higher MW SF. In addition, because of shorter SF chains, there is the presence of higher C-terminus carboxylic acid reactive sites in the lower MW SF which enhances GlcN substitutions. The order of GlcN substitution in the different reaction pathways were expected as this follows the trend of the number of reactive sites for conjugation (i.e. —COOH groups) present.

Figure 3F:
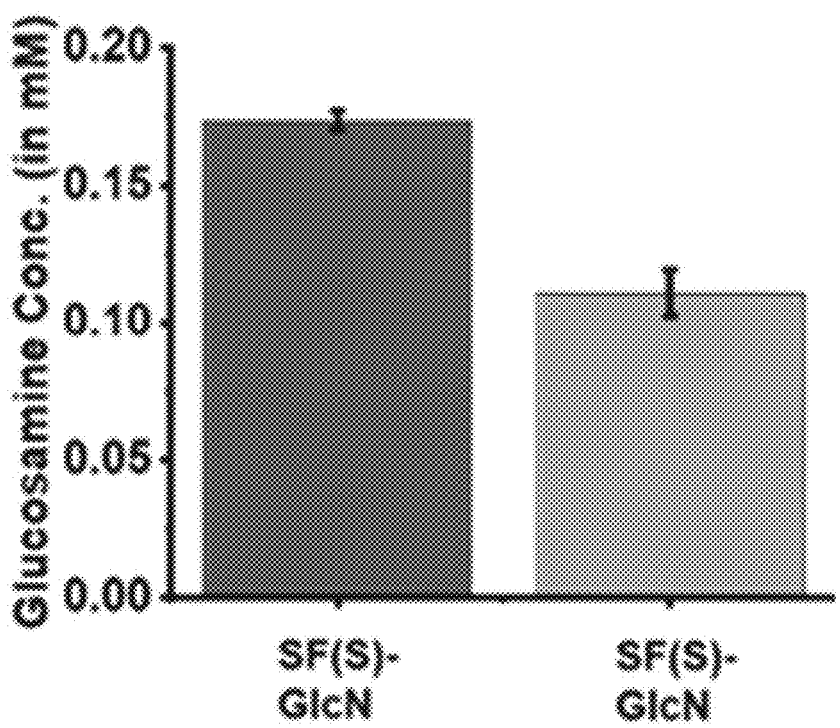
FIG. 3F is a comparison of glucosamine substitution in homogeneous and heterogenous reaction condition in same modification pathway (pathway 1). Freshly regenerated 79 kDa MW SF (homogeneous-left) and one month aged (heterogeneous-right) were used for glucosamine modification in similar reaction pathway and condition and substituted glucosamine was quantified and compared. Glucosamine substitutes significantly more in homogeneous reaction environment. Data are presented as mean±standard deviation; n=3, ***p<0.001 by one-way ANOVA with Tukey's post hoc test and unpair t test.

4. Quantification and Comparison of Saccharide Substitution onto Homogenous vs. Heterogeneous Reaction Modes by Mass Spectroscopy The effect of homogeneous (free chains) and heterogeneous (aggregated chains) reaction conditions on substitution efficiency with GlcN was investigated by comparing freshly regenerated (random chains) and one-month aged SF (some aggregation) as starting polymers. Low MW SF (79 kDa) and pathway 1 was chosen for this experiment as substitution reactions occur most efficiently (FIG. 3E). For homogeneous reactions, 79 kDa MW SF was used immediately after preparation, whereas for heterogeneous reactions, the same SF polymer was used one-month after preparation. FIG. 3F compares the GlcN substitutions in mM in the homogeneous and heterogeneous reaction conditions; 0.17±0.003 mM in homogeneous conditions (green) whereas heterogenous reactions were 0.11±0.008 mM. The difference in GlcN substitution was significant for both reaction environments.

The decrease in GlcN substitution in heterogeneous mode was expected and is likely related to chain aggregation over time in aged SF[67], resulting in decrease accessibility of some reactive sites for carboxylation and subsequent GlcN conjugation. This result indicates the GlcN substitution on silk chains not only depends on the modification pathways, but also the reaction mode and conditions of the starting polymer.

Figure 4C:
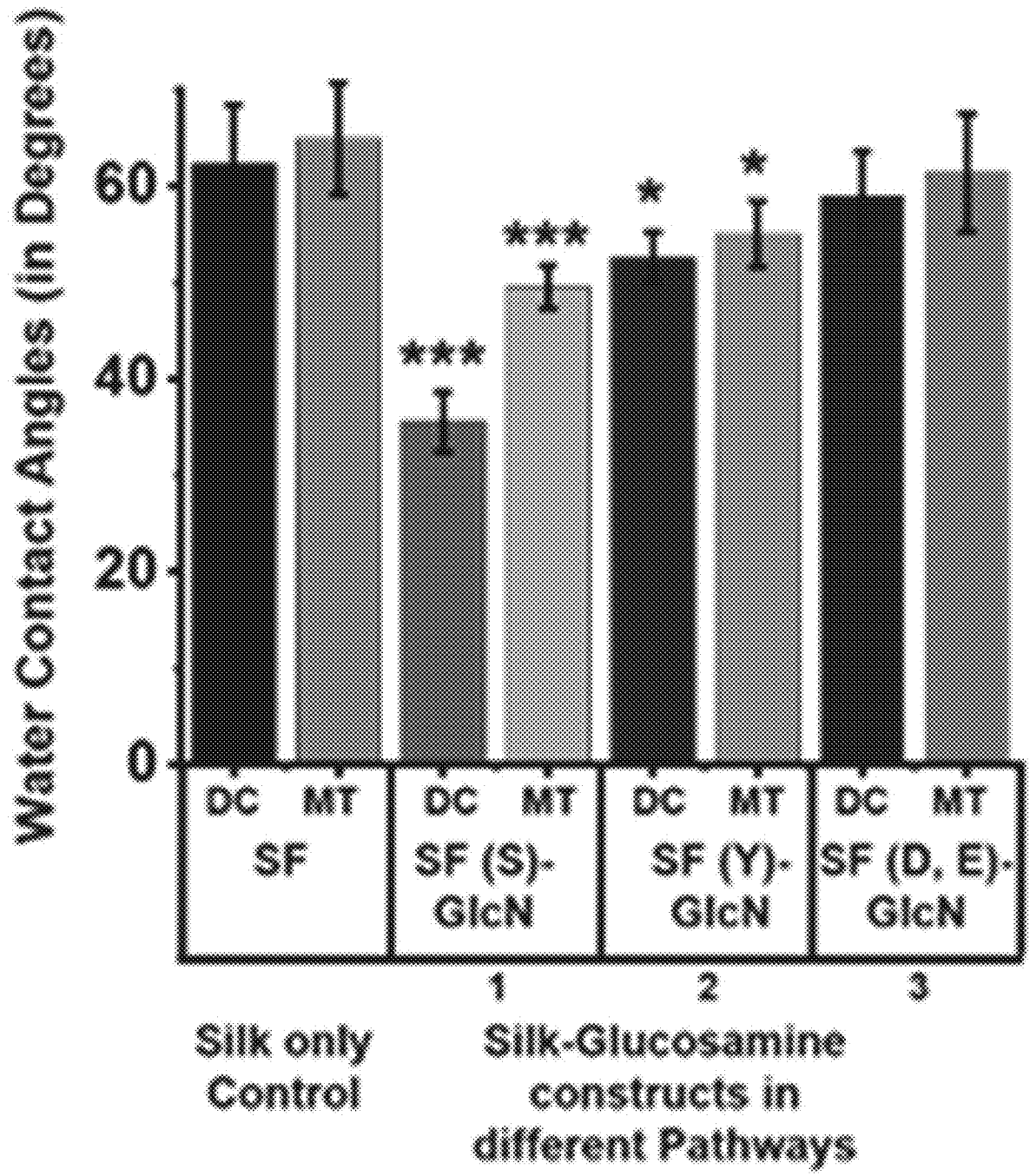
FIG. 4C shows WCA of different regenerated SF and SF-GlcN films prepared as cast (DC: direct cast) and methanol treated (MT) from SF of MW 157 kDa. Data are presented as mean±standard deviation (n=4). *p<0.033, p<0.002, *p<0.001 compared to control silk fibroin films by two-way ANOVA with Tukey's post hoc test.
Figure 4D:
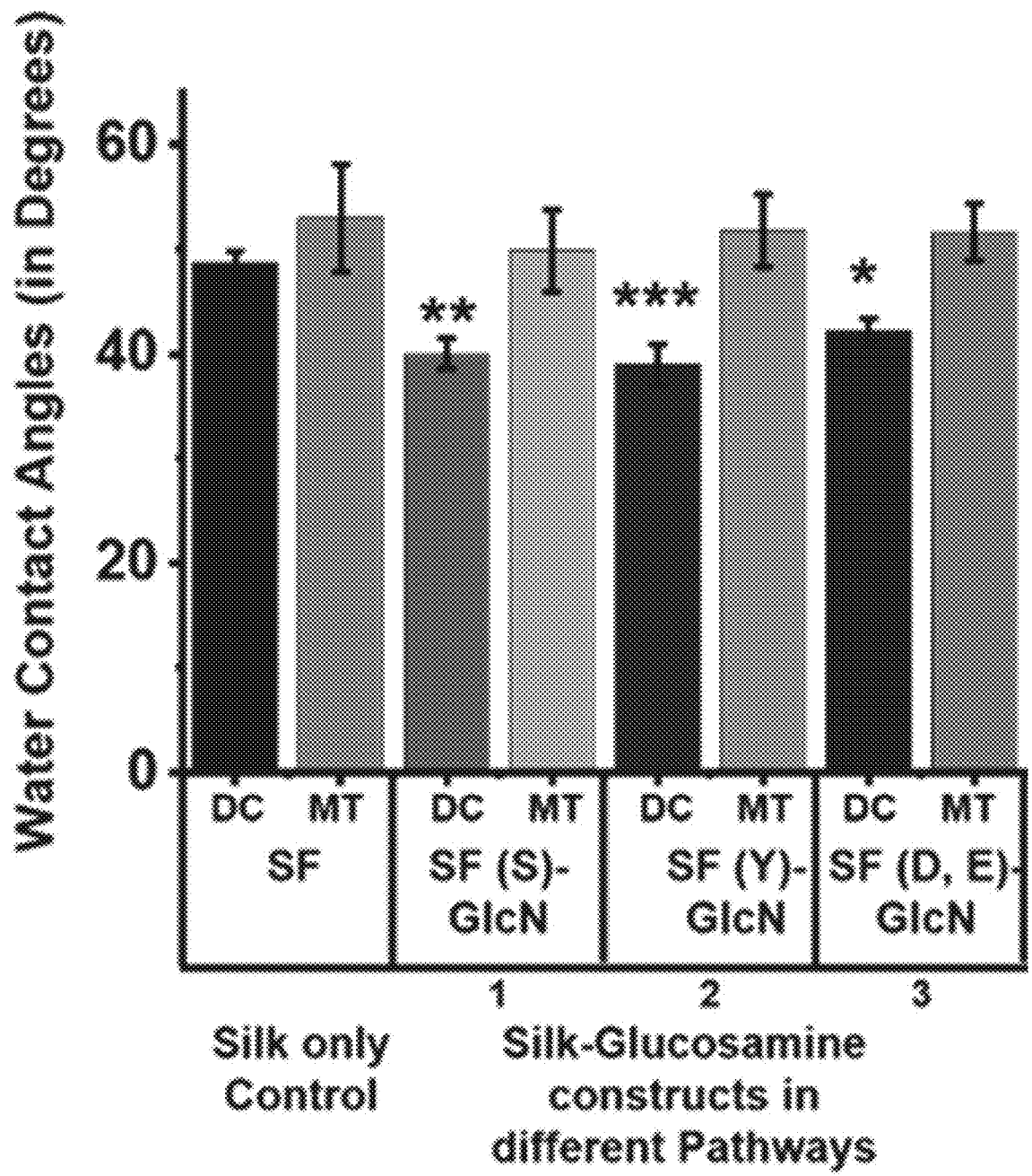
FIG. 4D shows WCA of different regenerated SF and SF-GlcN films prepared as cast (DC: direct cast) and methanol treated (MT) from SF of MW 79 kDa. Data are presented as mean±standard deviation (n=4). *p<0.033, p<0.002, *p<0.001 compared to control silk fibroin films by two-way ANOVA with Tukey's post hoc test.

5. Analysis of the Effect of Saccharide Functionalization on Surface Properties of Silk Fibroin by Water Contact Angle Measurements The changes in hydrophobicity/hydrophilicity of the SF-GlcN constructs, synthesized in the different pathways, were quantified using water contact angle (WCA) and compared with the as synthesized native SF solutions. FIGS. 4(A-D) summarize the WCA of as cast and methanol treated SF and SF-GlcN films prepared from the different MW distributions and pathways. For 157 kDa MW SF, WCA of as cast unmodified SF film was 62.4±6.05, whereas WCA of as cast SF(S)-GlcN (pathway 1), SF(Y)-GlcN (pathway 2) and SF(D, E)-GlcN (pathway 3) was 35.5±3.06, 52.6±2.6, 58.9±4.65 respectively.

After methanol treatment, WCA increased as the films were more hydrophobic as methanol induced β-sheet (crystal) formation[12, 68] that renders aqueous insolubility to the film surface. The WCA of methanol treated films were 64.9±5.77, 49.6±2.19, 55.1±3.43, 61.4±6.09 for SF, SF(S)-GlcN (pathway 1), SF(Y)-GlcN (pathway 2) and SF(D, E)-GlcN (pathway 3), respectively. The changes in WCA for SF(S)-GlcN and SF(Y)-GlcN were statistically significant in comparison to regenerated SF for both as cast and methanol treated films.

Similarly, for lower MW distribution SF (79 kDa), WCA of as cast unmodified SF was 48.7±1.15, whereas WCA of as cast SF(S)-GlcN (pathway 1), SF(Y)-GlcN (pathway 2) and SF(D, E)-GlcN (pathway 3) was 40.0±1.14, 39.0±1.94, 42.2±1.2, respectively. After methanol treatment, WCA increased as observed for higher MW SF (157 kDa). The WCA of methanol treated films were 53.0±5.18, 49.9±3.9, 51.8±3.43, 51.7±2.69 for SF, SF(S)-GlcN (pathway 1), SF(Y)-GlcN (pathway 2) and SF(D, E)-GlcN (pathway 3), respectively. The changes in WCA for SF(S)-GlcN and SF(Y)-GlcN, SF (D, E)-GlcN were significant in comparison to regenerated SF for DC films, whereas changes in WCA of methanol treated films were not statistically significant. The significant decrease in the water contact angle of DC films for SF(S)-GlcN in pathway 1 (for both MWs) in comparison to SF, could be attributed to chain scission (during the carboxylation, step 1, pathway 1) and GlcN substitution, which increases hydrophilicity, thereby decreasing the WCA significantly. In the case of SF(Y)-GlcN in pathway 2 (for both MWs), the decrease in WCA of the constructs in comparison to SF was relatively low compared to the pathway 1 constructs. The decrease can be attributed to the introduction of GlcN which introduces hydrophilicity. The decrease in WCA was more significant in SF with low MW (79 kDa) as higher GlcN substitution renders hydrophilicity to the film surface (FIG. 3D, FIG. 3E).

Like pathway 2, the decrease in WCA of pathway 3 constructs (SF (D, E)-GlcN) for both MWs SF, could be attributed to the GlcN substitution. The decrease was significant the low MW SF in the case of DC films (79 kDa), which could be related to higher GlcN substitution onto the protein polymer (FIG. 3D, FIG. 3E). These findings indicate the significance of the GlcN functionalization onto silk polymer and its effect on the surface hydrophilicity/hydrophobicity of films. In addition, the synthetic pathways significantly influenced overall hydrophilicity, with higher GlcN substitution resulting in lower WCA.

Figure 5D:
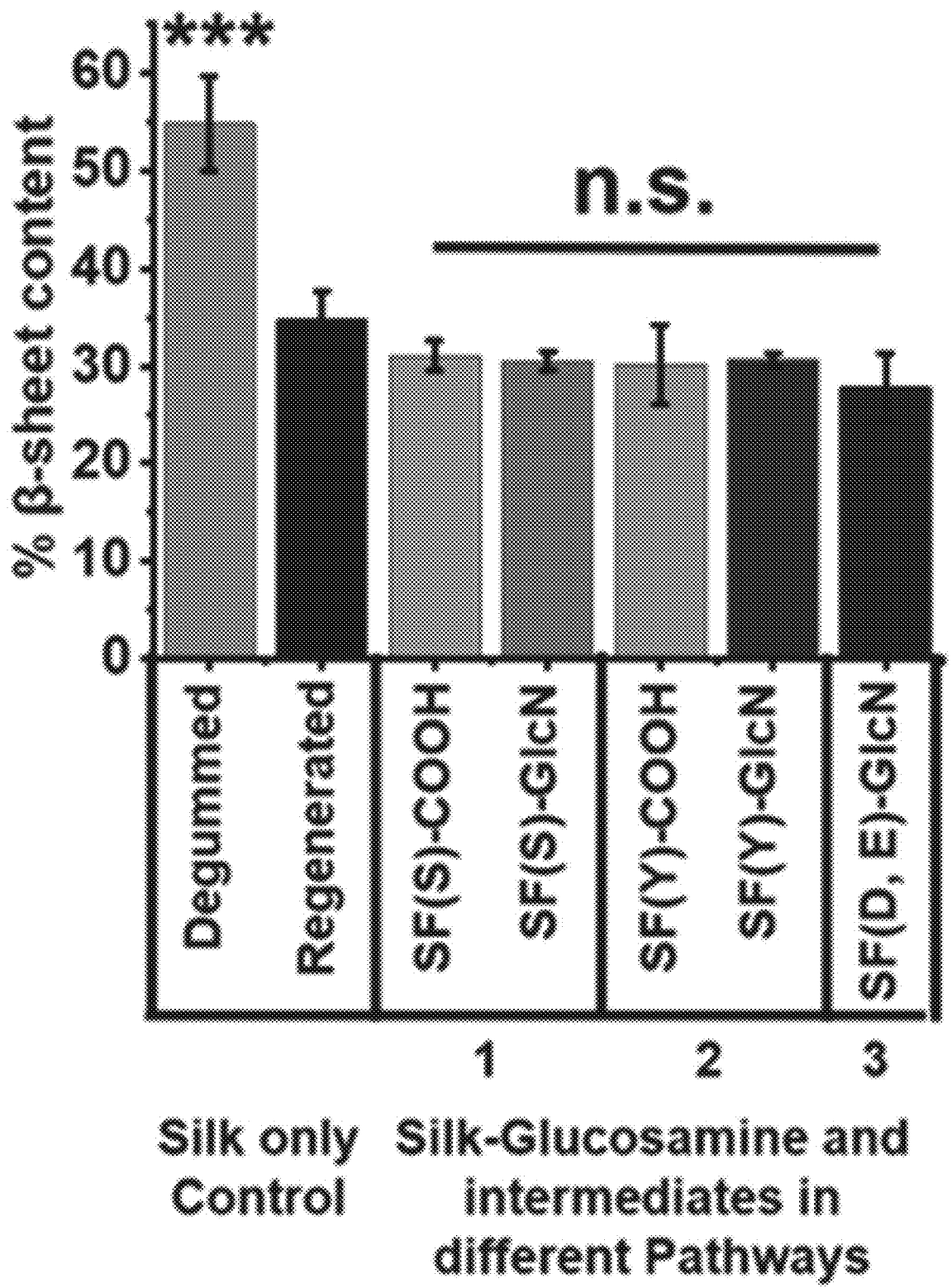
FIG. 5D shows percentage β-sheet content in degummed and regenerated SF, reaction intermediates and as synthesized SF-GlcN lyophilized powders, synthesized in different modification Pathways starting from 157 kDa MW SF. Data are presented as mean±standard deviation (n=3). ***$p<0.001$ compared to control regenerated silk fibroin by one-way ANOVA with Bonferroni multiple comparison test.
Figure 5E:
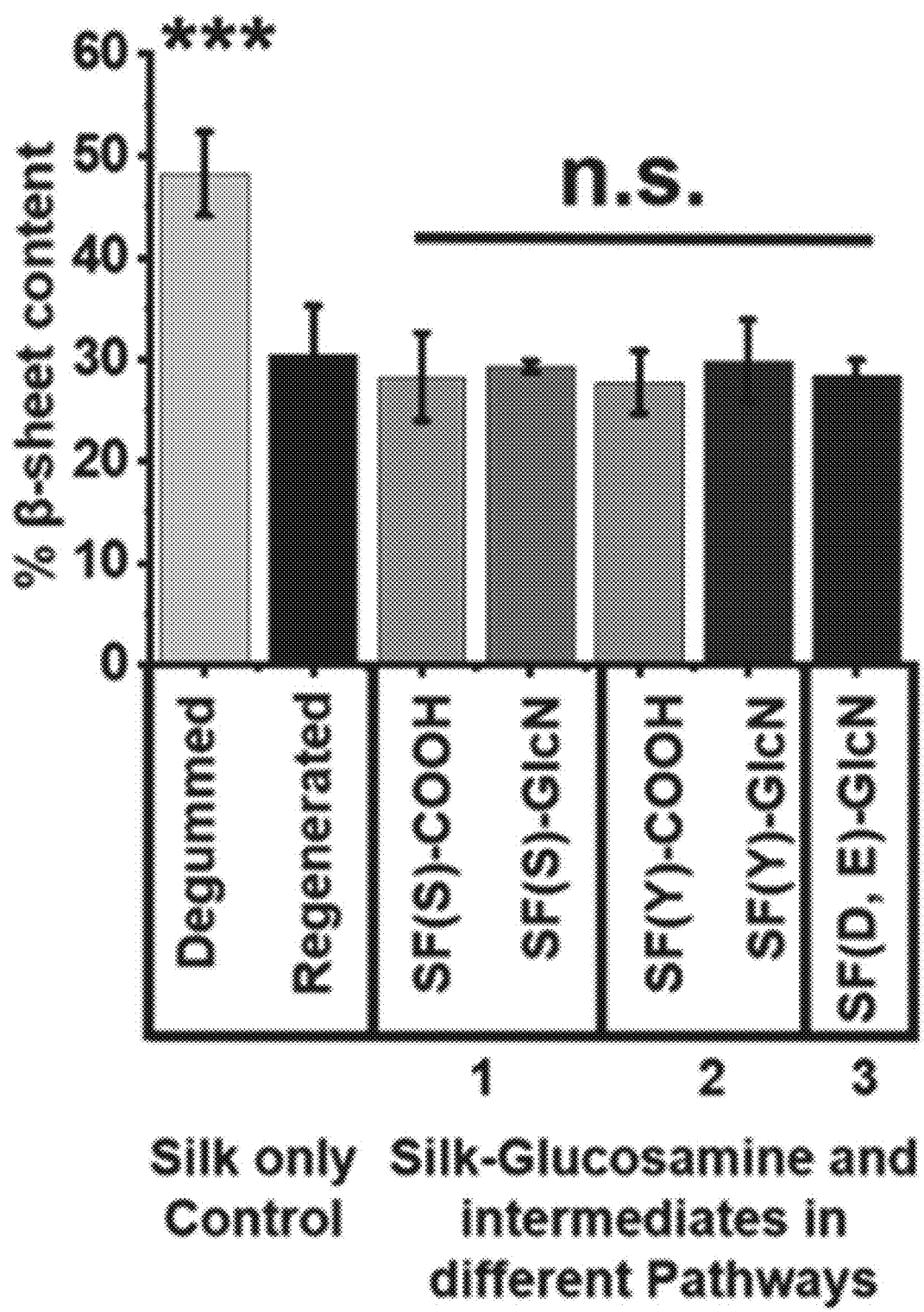
FIG. 5E shows percentage β-sheet content in degummed and regenerated SF, reaction intermediates and as synthesized SF-GlcN lyophilized powders, synthesized in different modification Pathways starting from 79 kDa MW SF. Data are presented as mean±standard deviation (n=3). ***$p<0.001$ compared to control regenerated silk fibroin by one-way ANOVA with Bonferroni multiple comparison test.

6. Analysis of the Secondary Structures of the Sugar Substituted Silk Fibroin by Fourier Transform Infrared (FTIR) Spectroscopy SF is a semi-crystalline natural polymer which consists of β-sheet nanocrystals embedded in a relatively less-organized matrix.[69] The superior structural support and excellent mechanical properties of SF can be attributed to these β-sheet crystals, due to the strong hydrogen bonding network.[69-70] In order to enhance aqueous solubility, silk degummed fibers are treated with concentrated lithium bromide (LiBr) solution, which breaks the strong hydrogen bonded network.[71] In the present examples, multiple chemistries (e.g. nucleophilic substitution, conjugation, diazonium coupling) were used with regenerated SF to realize GlcN incorporation onto SF polymer. Attenuated total reflectance fourier transform infrared (ATR-FTIR) spectroscopy was performed to clarify changes in secondary structures (FIG. 5(A-E)). FT-IR was performed on as synthesized lyophilized powders of SF-GlcN constructs (starting from 157 and 79 kDa MW SF). Degummed and regenerated SF of both MWs were used as controls. The digital images of the lyophilized powders are provided in FIG. 5A. FIG. 5B and FIG. 5C represent the FT-IR spectra of the degummed SF, regenerated SF, SF-GlcN with the multiple pathways and their reaction intermediates starting from 157 and 79 kDa MW SF, respectively.

There was a strong absorption peak at 1617 $cm^{-1}$ in the FTIR spectrum for degummed SF of both MWs which corresponds to the β-sheet structure. However, in case of regenerated SF, SF-GlcN constructs and reaction intermediates, there was a change in peak position in the FTIR spectra with strong absorption peak at 1644 $cm^{-1}$ attributed to random coils. In the amide I region (1700-1600 $cm^{-1}$), the bands at 1637-1616 $cm^{-1}$ and 1703-1697 $cm^{-1}$ are assigned to the β-sheets structures.[72] For the 157 kDa MW SF, the percentage of β-sheet was 54.83±4.85, 34.78±2.94, 31.09±1.53, 30.6±0.95, 30.19±4.07, 30.72±0.66, 27.86±3.48 for degummed SF, regenerated SF, SF(S)—COOH, SF(S)-GlcN, SF(Y)—COOH, SF(Y)-GlcN, SF(D, E)-GlcN, respectively.

Similarly, for the 79 kDa MW SF, the percentage of β-sheet was 48.26±4.1, 30.48±4.85, 28.35±4.34, 29.36±0.56, 27.75±3.13, 29.87±4.03, 28.46±1.54 for degummed SF, regenerated SF, SF(S)—COOH, SF(S)-GlcN, SF(Y)—COOH, SF(Y)-GlcN, SF(D, E)-GlcN, respectively. The ATR-FTIR spectra and percentage β-sheet content showed no significant differences between modified constructs (all SF-GlcN and intermediates) and regenerated SF across the two MWs. However, as expected, there was a significant difference in the percentage β-sheet content of regenerated and degummed SF. These findings indicate that the multiple chemistries and reaction environments did not significantly alter the final β-sheet (crystalline) content in comparison to regenerated SF. Thus, the structural identity of the protein polymer was preserved, with the sugar modifications.

7. Processability of the Silk-sugar Constructs into Multiple Material Formats

Figure 6A:
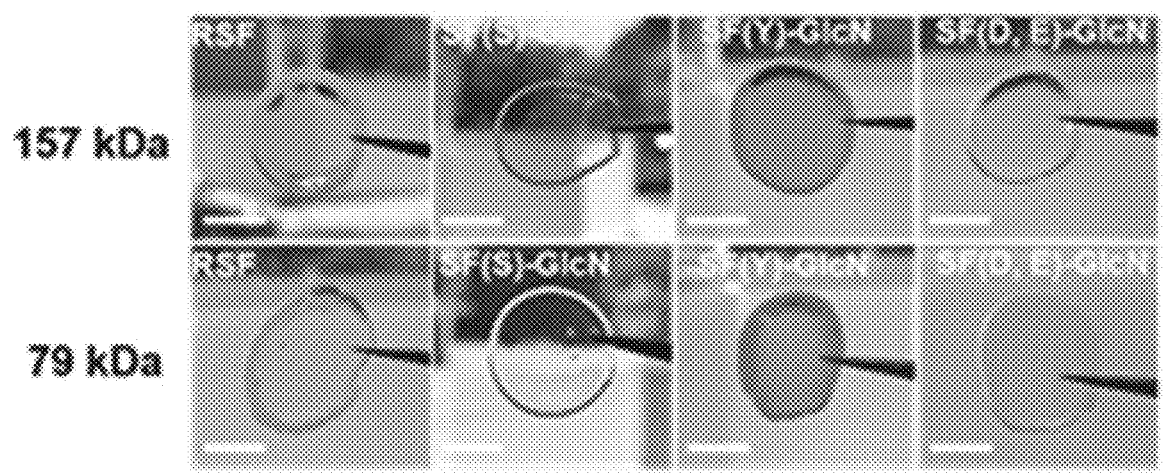
FIG. 6A shows digital images of regenerated SF and SF-GlcN films. Films were prepared from 3 wt % aqueous solutions, drop casting them in polydimethyl siloxane (PDMS) mold at room temperature and drying them overnight in a fume hood. Scale bar: 1 cm.

To assess these biomaterials for biomedical applications, aqueous processability into functional material formats, such as films and sponges was assessed. Films[73-74] and sponges[75-76] are useful as scaffolds for different tissue engineering applications, including as mimics of the physiological niche.[77] Digital micrographs of as prepared films from the different SF-GlcN constructs, as well as a regenerated SF (control) are shown in FIG. 6A. The dried films were treated with methanol overnight to induce β-sheet and render water insolubility. The formation of β-sheets and its content in direct cast and methanol treated SF-GlcN films, along with the control films, were assessed using FTIR spectroscopy (FIG. 6C, FIG. 6D, FIG. 6G, FIG. 6H). Direct cast films of SF-GlcN constructs (from all pathways) of both SF MW distributions and control SF films showed strong peaks at 1644 $cm^{-1}$, corresponding to random coil.

However, after methanol treatment, all the films showed a maximum absorption peak at 1620 $cm^{-1}$ indicating a conformational transition from random coil to β-sheet due to the methanol treatment.[12, 68] The percentage β-sheet content in films before and after methanol treatment were analyzed by fourier self-deconvolution. For 157 kDa MW SF, percentage β-sheet contents were 35.22±1.67, 48.63±2.52, 31.97±2.23, 43.71±3.36, 34.51±2.16, 43.45±1.51, 37.08±0.84, 45.56±5.17 for SF (DC), SF(MT), SF(S)-GlcN (DC), SF(S)-GlcN (MT), SF(Y)-GlcN (DC), SF(Y)-GlcN (MT), SF(D, E)-GlcN (DC), SF(D, E)-GlcN (MT), respectively. Similarly, for 79 kDa MW SF, the percentage of β-sheet content was 36.68±1.14, 45.57±3.71, 33.03±4.38, 47.16±1, 35.53±1.89, 48.43±0.75, 37.75±1.4, 45.47±5.27 for SF (DC), SF(MT), SF(S)-GlcN (DC), SF(S)-GlcN (MT), SF(Y)-GlcN (DC), SF(Y)-GlcN (MT), SF(D, E)-GlcN (DC), SF(D, E)-GlcN (MT), respectively. Significant differences between β-sheet contents were detected for each film except SF (D, E)-GlcN (79 kDa MW) before and after methanol treatment.

Figure 6B:
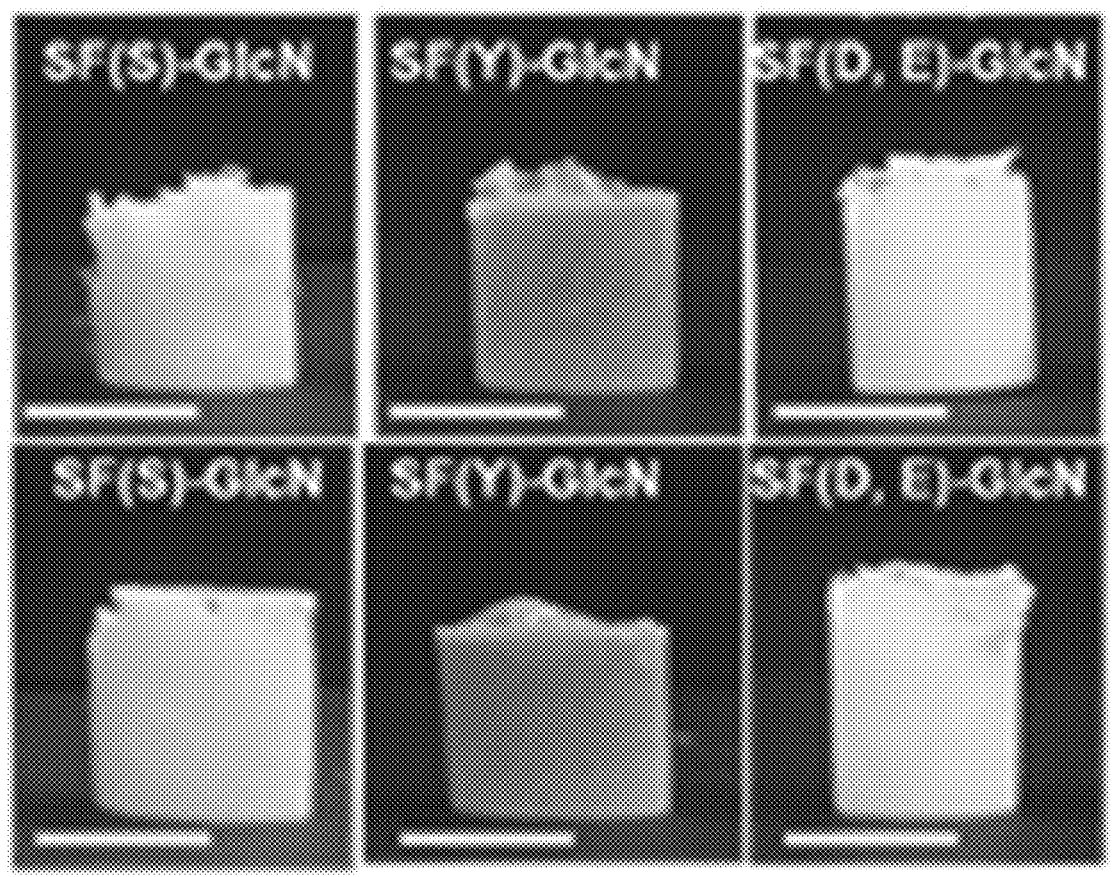
FIG. 6B shows digital images of SF-GlcN sponges as prepared (AP) from 8 wt % aqueous solutions of SF-GlcN powders. Sponges were obtained by freezing the aqueous solutions at −20° C. overnight, followed by lyophilizing for 72 h. Scale bar: 1 cm.
Figure 6C:
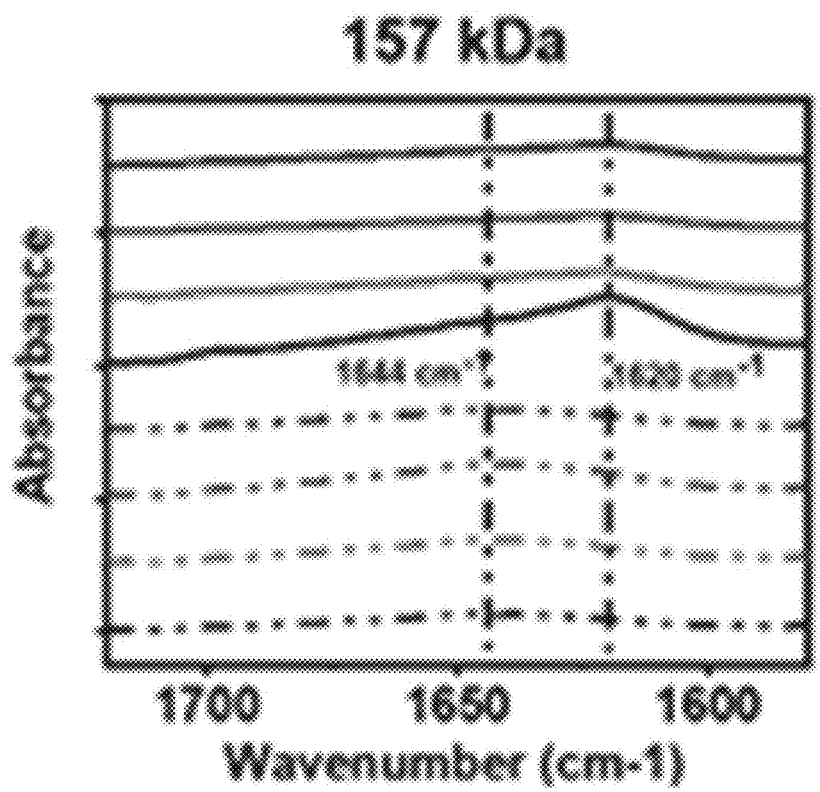
FIG. 6C shows FT-IR spectra of regenerated SF, SF-GlcN films from each pathway starting from 157 kDa before and after methanol treatment. For direct cast (DC) films, strong FT-IR absorption peak was observed at 1644 $cm^{-1}$ corresponding to random coil structure. After methanol treatment (MT), strong FT-IR absorption peak at 1620 $cm^{-1}$ corresponding to β-sheet structure was observed. For FIGS. 6C, 6D, 6E, and 6F, the plots are, from the top down: SF(D, E)-GlcN (MeOH treated)—top; SF(Y)-GlcN (MeOH treated); SF(S)-GlcN (MeOH treated); SF (MeOH treated); SF(D, E)-GlcN; SF(Y)-GlcN; SF(S)-GlcN); and SF—bottom.
Figure 6D:
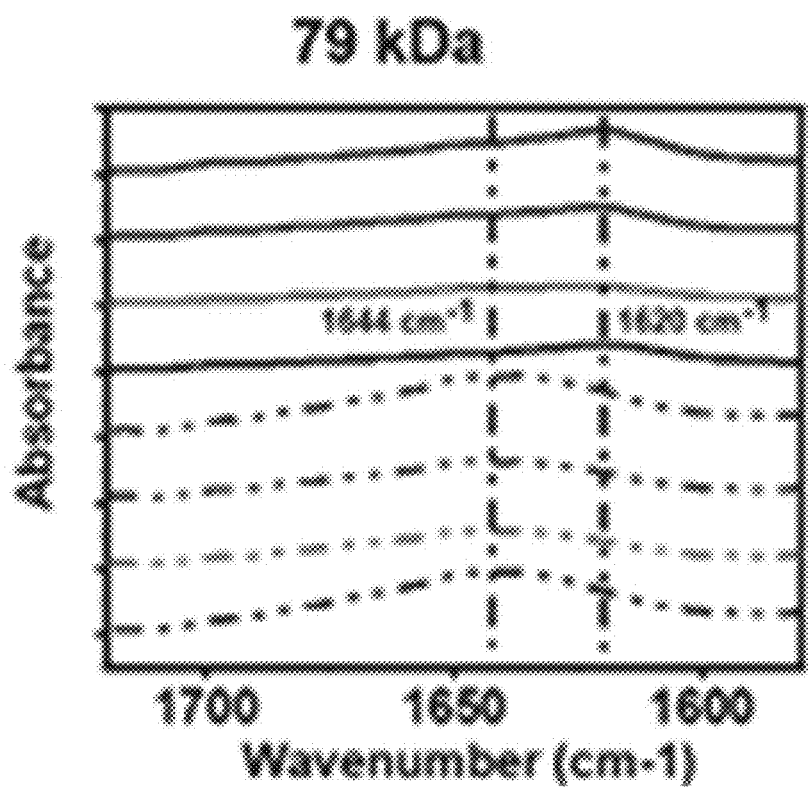
FIG. 6D shows FT-IR spectra of regenerated SF, SF-GlcN films from each pathway starting from 79 kDa before and after methanol treatment. For direct cast (DC) films, strong FT-IR absorption peak was observed at 1644 $cm^{-1}$ corresponding to random coil structure. After methanol treatment (MT), strong FT-IR absorption peak at 1620 $cm^{-1}$ corresponding to β-sheet structure was observed.
Figure 6E:
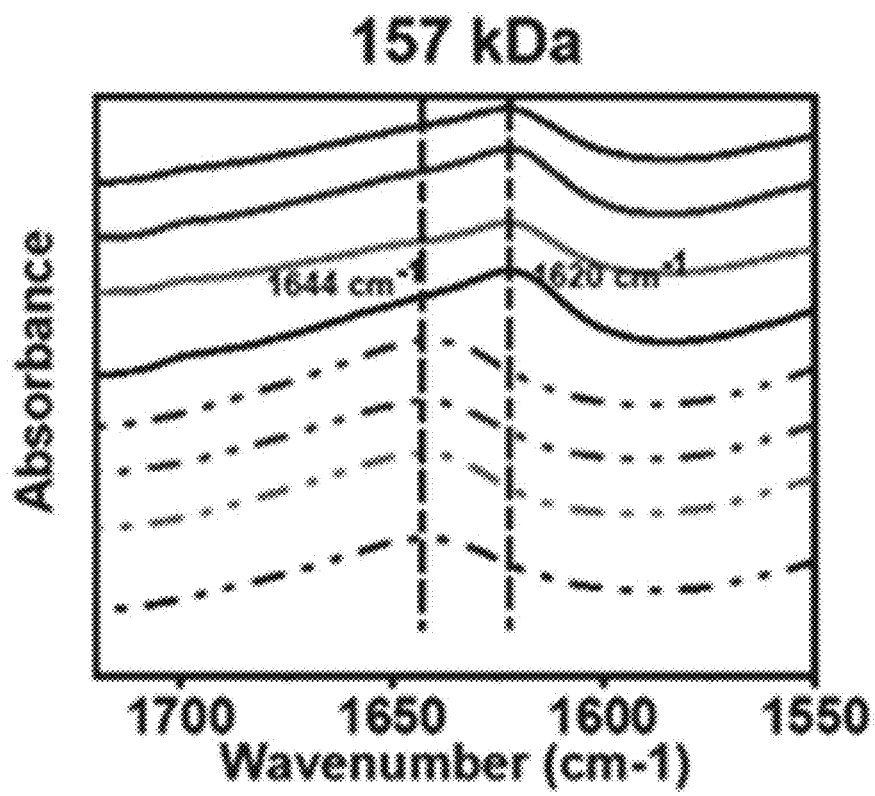
FIG. 6E shows FT-IR spectra of regenerated SF, SF-GlcN sponges from each pathway starting from 157 kDa SF before and after methanol treatment. Like films, strong absorptions at 1644 and 1620 $cm^{-1}$ were observed for sponges before and after methanol treatment respectively.
Figure 6F:
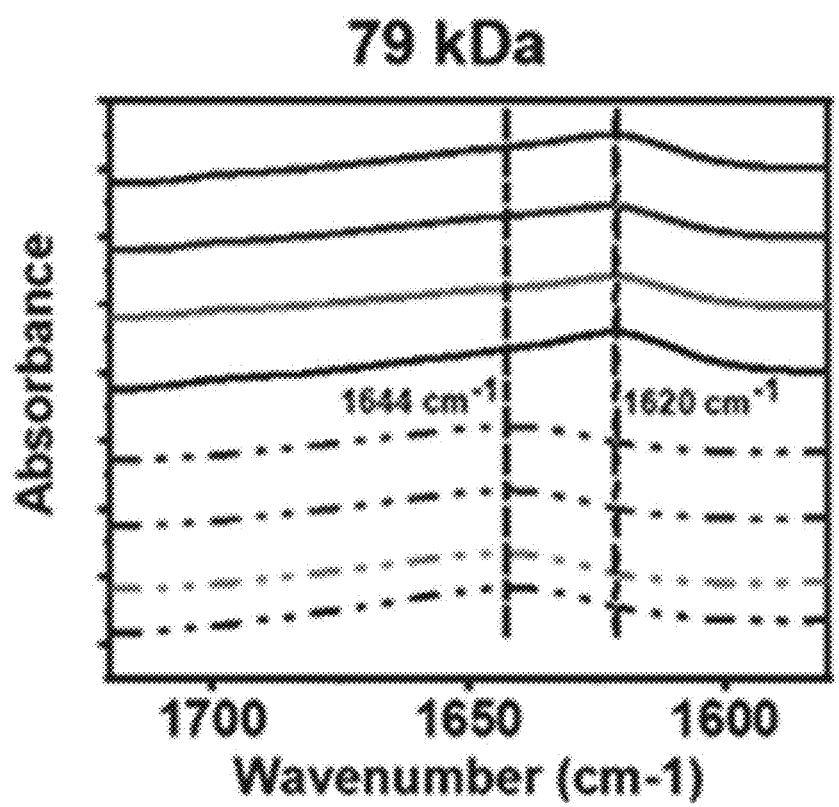
FIG. 6F shows FT-IR spectra of regenerated SF, SF-GlcN sponges from each pathway starting from 79 kDa SF before and after methanol treatment Like films, strong absorptions at 1644 and 1620 $cm^{-1}$ were observed for sponges before and after methanol treatment respectively.
Figure 6H:
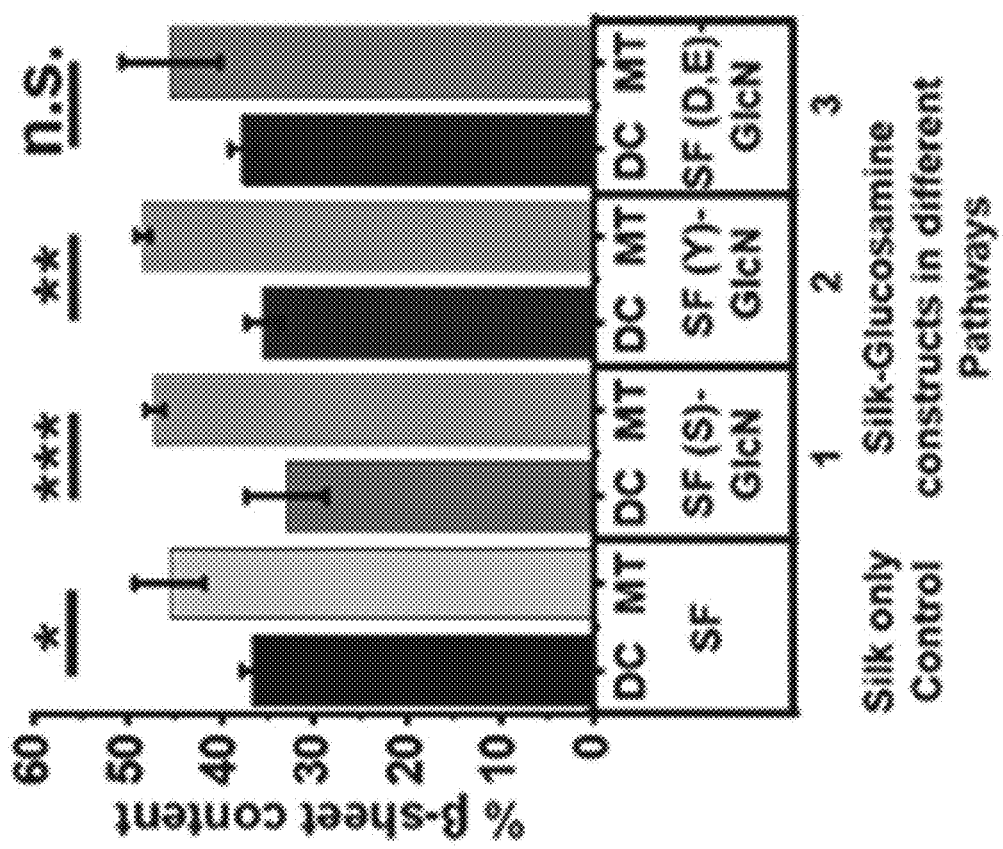
FIG. 6H shows percentage β-sheet content of SF and SF-GlcN films from each pathway starting from 79 kDa SF before and after methanol treatment.
Figure 6G:
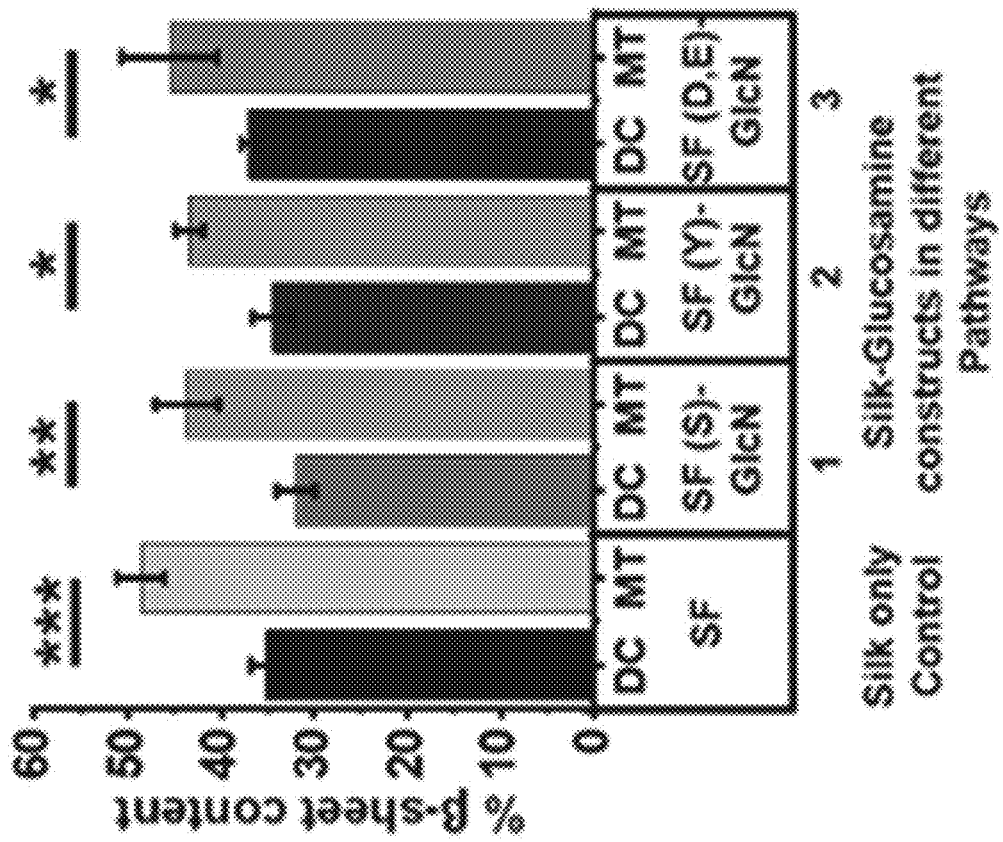
FIG. 6G shows percentage β-sheet content of SF and SF-GlcN films from each pathway starting from 157 kDa SF before and after methanol treatment.
Figure 6I:
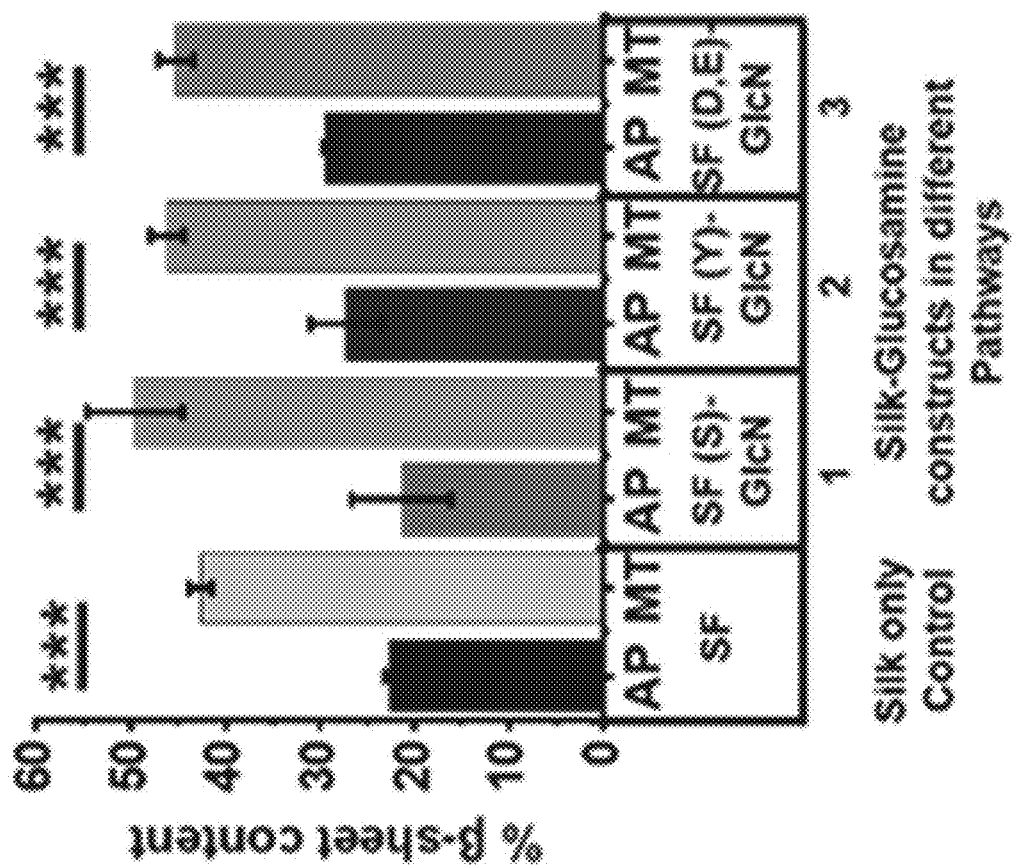
FIG. 6I shows β-sheet content of SF and SF-GlcN sponges prepared from each pathway starting from 157 kDa SF before and after methanol treatment. Data are presented as mean±standard deviation (n=3). *$p<0.03$, $p<0.002$, *$p<0.001$ by one-way ANOVA with Tukey's post hoc test.
Figure 6J:
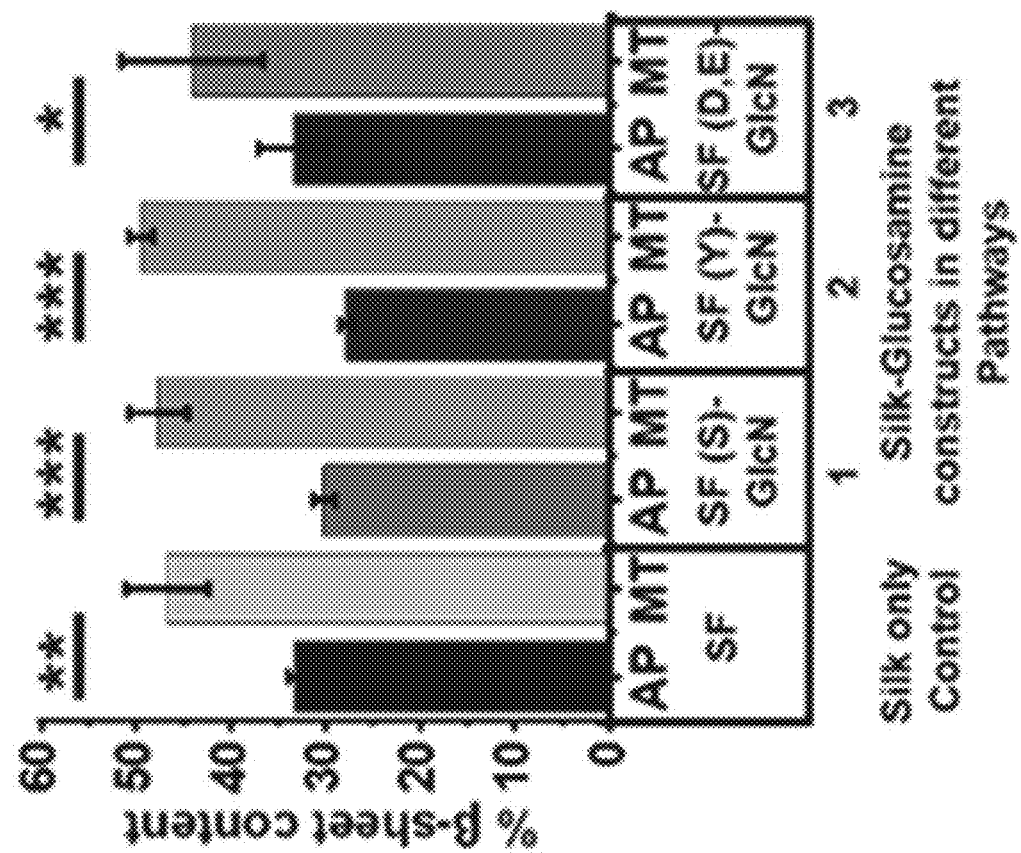
FIG. 6J shows β-sheet content of SF and SF-GlcN sponges prepared from each pathway starting from 79 kDa SF before and after methanol treatment. Data are presented as mean±standard deviation (n=3). *$p<0.03$, $p<0.002$, *$p<0.001$ by one-way ANOVA with Tukey's post hoc test.

Similarly, digital images of the SF-GlcN sponges are shown in FIG. 6B. After lyophilization, as prepared (AP) sponges were treated with methanol overnight to increase β-sheet content and confer water stability. The percentage of β-sheet content in the as prepared and methanol treated sponges, along with the control sponges, were analyzed by FTIR spectroscopy (FIG. 6E, FIG. 6F, FIG. 6I, FIG. 6J). As prepared (AP) sponges of SF-GlcN constructs (from all pathways) of both SF MW distributions and control SF sponges absorbed at 1644 $cm^{-1}$, attributed to random coil. However, after methanol treatment, the sponges showed strong absorption peaks at 1620 $cm^{-1}$ indicating inducement of β-sheets due to the methanol treatment.[68] For the 157 kDa MW SF as starting polymer, the percentage β-sheet contents were 33.3±0.7, 46.77±4.36, 30.18±1.23, 47.69±3.07, 27.8±0.69, 49.49±1.3, 33.42±3.75, 44.07±7.52 for SF (AP), SF(MT), SF(S)-GlcN (AP), SF(S)-GlcN (MT), SF(Y)-GlcN (AP), SF(Y)-GlcN (MT), SF(D, E)-GlcN (AP), SF(D, E)-GlcN (MT) sponges, respectively. Similarly, for the 79 kDa MW SF, the percentage β-sheet contents were 22.65±0.5, 42.68±1.21, 21.32±5.25, 49.56±5.02, 27.32±3.84, 46.16±1.81, 29.39±0.41, 45.28±1.85 for SF (AP), SF(MT), SF(S)-GlcN (AP), SF(S)-GlcN (MT), SF(Y)-GlcN (AP), SF(Y)-GlcN (MT), SF(D, E)-GlcN (AP), SF(D, E)-GlcN (MT) sponges, respectively. Significant differences between β-sheet content were detected for each sponge before and after the methanol treatment.

8. Biological Properties of the Silk-sugar Films and Sponges

Figure 7A:
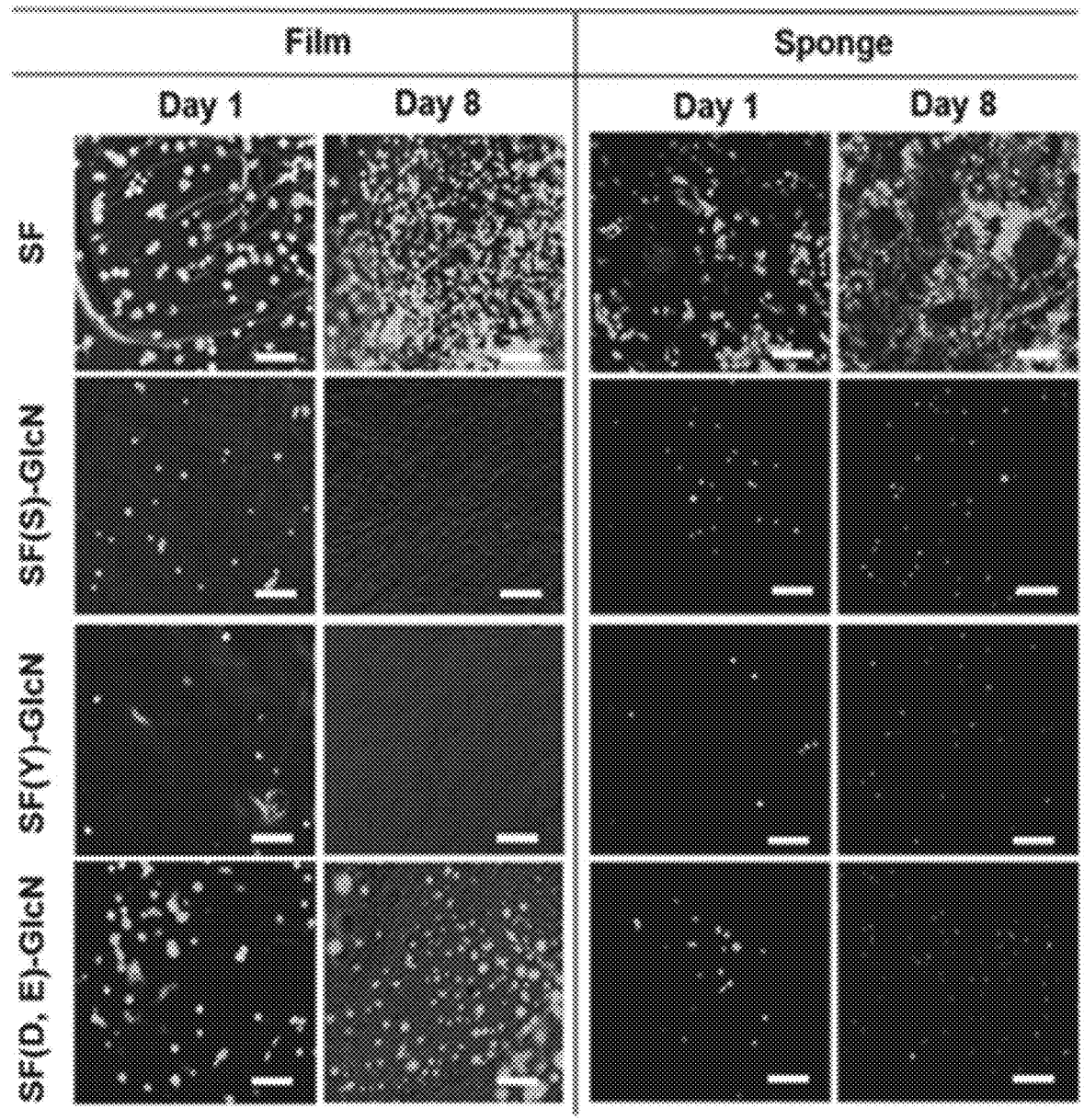
FIG. 7A shows fluorescent and CLSM micrographs of L929 murine fibroblast cultured on 157 kDa SF and SF-GlcN films or sponges, respectively, and live/dead stained at days 1 and 8. Green: calcein, red: ethidium homodimer-1. Scale bars: 100 μm Note: due to publication requirements in certain jurisdictions, these figures may not suitably distinguish between the two colored entities. A copy of this figure in color form can be provided to a patent examiner, if necessary. Alternatively, for a non-patent-examining reader, the color version of the figure can be located either in the provisional patent application to which this application claims priority or a journal publication that describes the experiments performed in the examples below and lists one or more of the co-inventors of this application as co-authors.
Figure 7B:
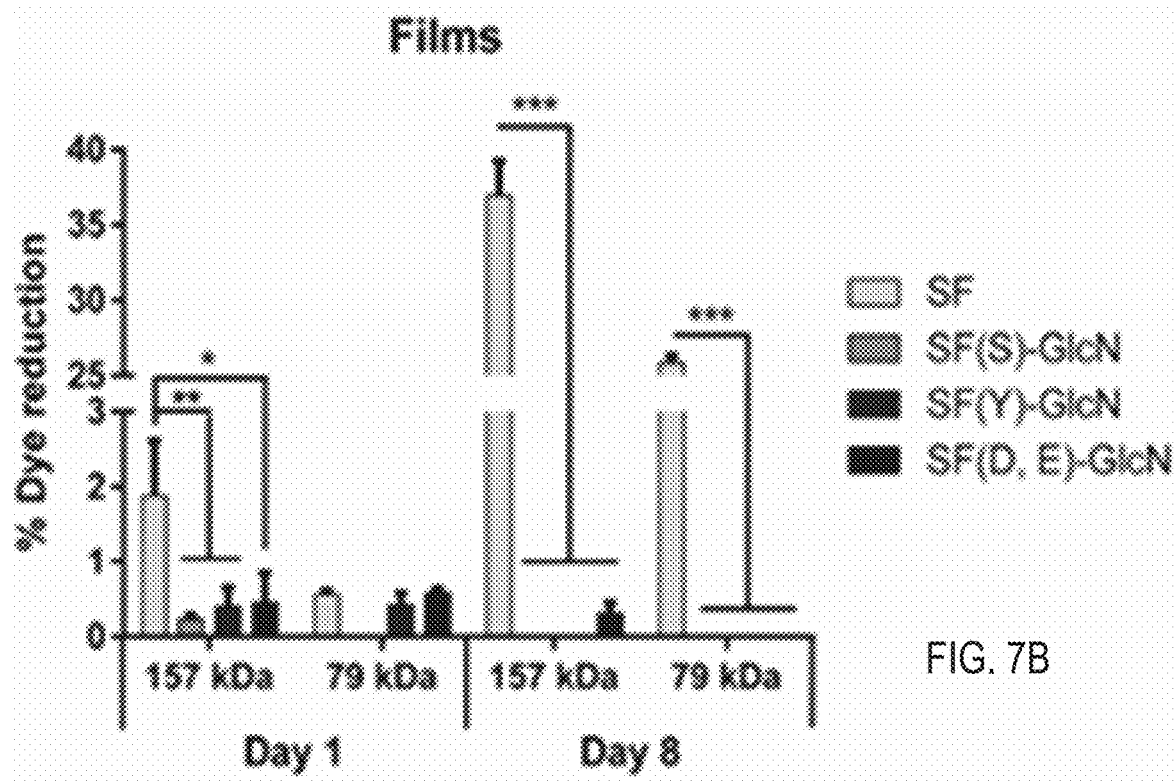
FIG. 7B shows relative metabolic activities of the cells on films determined by percent reduction of alamarBlue dye at days 1 and 8. Data are presented as mean±standard deviation (n=3). *$p<0.03$, $p<0.002$, *$p<0.001$ by one-way ANOVA with Tukey's post hoc test.
Figure 7C:
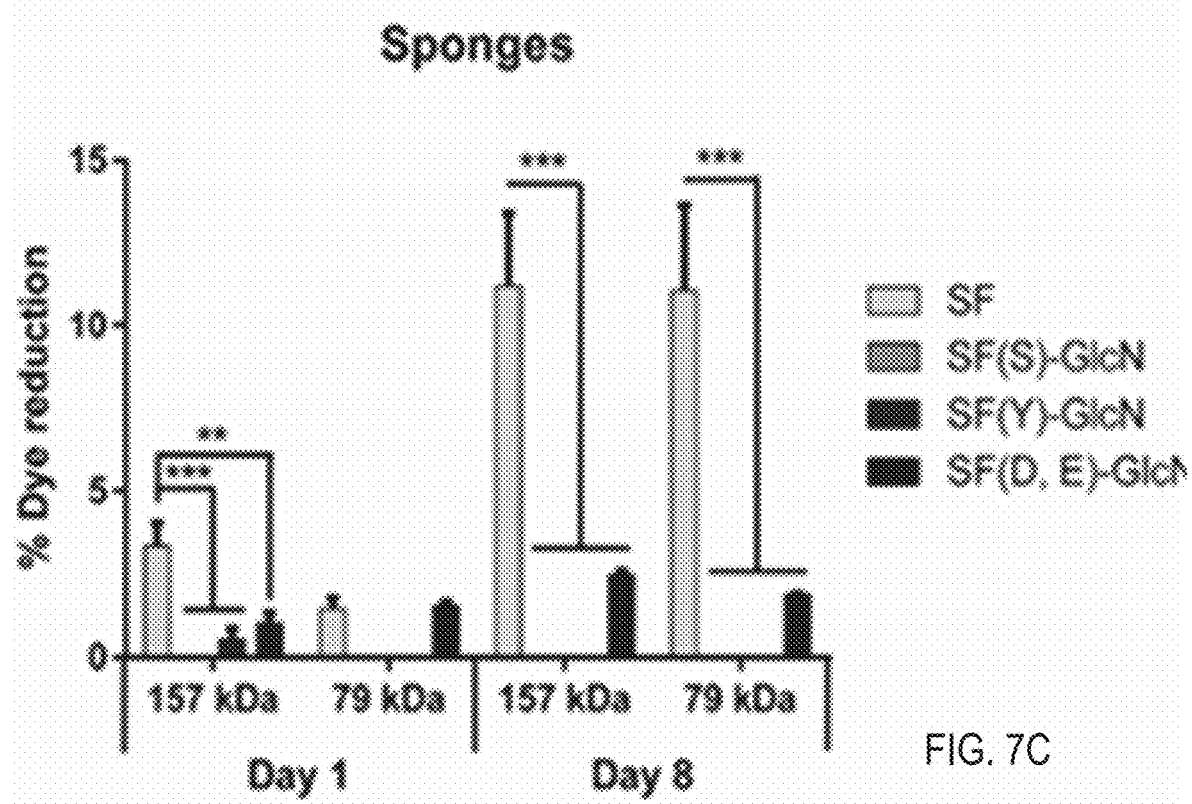
FIG. 7C shows relative metabolic activities of the cells on sponges determined by percent reduction of alamarBlue dye at days 1 and 8. Data are presented as mean±standard deviation (n=3). *$p<0.03$, $p<0.002$, *$p<0.001$ by one-way ANOVA with Tukey's post hoc test.

The response of L929 murine fibroblasts cultured on SF and SF-GlcN films or sponges was monitored over 8 days to assess cytocompatibility. Cell density and metabolic activity increased significantly on both the 157 kDa or 79 kDa SF films and sponges over 8 days (FIG. 7(A-C)), indicating support for cell growth. Substitution of GlcN moieties, however, impaired cell attachment and proliferation, particularly on the serine and tyrosine-modified samples. A negative correlation was observed between GlcN concentration and metabolic activity on films (FIG. 7B) and sponges (FIG. 7C) at day 1, suggesting a negative impact of GlcN groups on cell attachment. Cells on SF(S)-GlcN and SF(Y)-GlcN films had a spherical shape and most were positive for EthD-1, implying loss of membrane integrity and cell death. Dye reduction on the 157 kDa SF(S)-GlcN and SF(Y)-GlcN films or sponges at day 8 also indicated low or no metabolic activity. Although there was no significant change in dye reduction on the 157 kDa SF (D, E)-GlcN films at day 8 compared to day 1, a slight increase was recorded on SF (D, E)-GlcN sponges over 8 days of culture. Similarly, no dye reduction was recorded on the 79 kDa SF (D, E)-GlcN films at day 8 while the metabolic activity was preserved on the corresponding sponges over 8 days. These results suggest that the 3D microstructure of the sponges supported better cell survival compared to 2D films.

Despite lacking cell recognition sequences[78], SF-based materials support cell attachment and growth.[14, 16, 63, 79-80] The impaired cell response to the GlcN-substituted SF materials is explained by the introduction of hydrophilic, uncharged GlcN moieties that resist protein adsorption and non-specific cell adhesion as reported for cellulose[81] or dextran.[38] Cell adhesion and growth improve the performance of tissue engineering scaffolds for many applications[82]. However, cell or tissue adhesion could be undesirable for specific biomaterial applications, such as gauzes or barriers used for preventing postoperative adhesion[83-84] or antithrombogenic prosthetic vascular grafts.[85] Thus, the GlcN-substituted SF could be a mechanically robust, more durable alternative to polysaccharide-based anti-adhesive materials such as heparin,[86] dextran,[87] cellulose[88] or alginate.[89] Moreover, adhesion of certain cell types with high affinity to glucose, such as macrophages with scavenger receptors,[90] hepatocytes with lectins[91] or leukocytes with glycoprotein binding receptors[92] could be upregulated on SF-based materials for in vitro models, the subject of future studies.

Robust, versatile chemical pathways were developed to incorporate GlcN onto silk chains of different MWs by leveraging different chemistries and conjugation strategies with control over GlcN substitution. GlcN conjugation was also explored in both homogeneous and heterogeneous modes and substitutions quantified and compared; homogeneous reactions had higher degrees of substitution than heterogeneous modes. The impact of GlcN substitution on different material properties, such as surface features, β-sheet content, processability into different material formats, cell viability and metabolic activity was investigated. High GlcN substitution significantly reduced cell attachment and growth on films and sponges, revealing anti-adhesive properties. These findings provide new options to libraries of new biomaterials based on silk (and other natural biopolymers such as silk-elastin like polymer (SELPs) with sugars, which could find applications in a broad range of biomedical needs as anti-adhesive materials, mimics of complex tissue systems, and as drug delivery matrices, among others. In addition, natural biopolymers modified with sugars could offer unique opportunities to generate surface features with control over biofouling as biomimetic coating materials.

REFERENCES

1. Murphy, A. R.; Kaplan, D. L., Biomedical applications of chemically-modified silk fibroin. *Journal of materials chemistry* 2009, 19 (36), 6443-6450.
2. Vepari, C.; Kaplan, D. L., Silk as a biomaterial. *Progress in polymer science* 2007, 32 (8-9), 991-1007.
3. Altman, G. H.; Diaz, F.; Jakuba, C.; Calabro, T.; Horan, R. L.; Chen, J.; Lu, H.; Richmond, J.; Kaplan, D. L., Silk-based biomaterials. *Biomaterials* 2003, 24 (3), 401-416.
4. Cao, Y.; Wang, B., Biodegradation of silk biomaterials. *International journal of molecular sciences* 2009, 10 (4), 1514-1524.
5. Kundu, B.; Kurland, N. E.; Bano, S.; Patra, C.; Engel, F. B.; Yadavalli, V. K.; Kundu, S. C., Silk proteins for biomedical applications: Bioengineering perspectives. *Progress in polymer science* 2014, 39 (2), 251-267.
6. Shao, Z.; Vollrath, F., Surprising strength of silkworm silk. *Nature* 2002, 418 (6899), 741-741.
7. Jin, H.-J.; Kaplan, D. L., Mechanism of silk processing in insects and spiders. *Nature* 2003, 424 (6952), 1057-1061.

8. Pritchard, E. M.; Kaplan, D. L., Silk fibroin biomaterials for controlled release drug delivery. *Expert opinion on drug delivery* 2011, 8 (6), 797-811.
9. Kim, H. J.; Kim, U. J.; Leisk, G. G.; Bayan, C.; Georgakoudi, I.; Kaplan, D. L., Bone regeneration on macroporous aqueous-derived silk 3-D scaffolds. *Macromolecular bioscience* 2007, 7 (5), 643-655.
10. Wang, Y.; Blasioli, D. J.; Kim, H.-J.; Kim, H. S.; Kaplan, D. L., Cartilage tissue engineering with silk scaffolds and human articular chondrocytes. *Biomaterials* 2006, 27 (25), 4434-4442.
11. Wang, Y.; Kim, U.-J.; Blasioli, D. J.; Kim, H.-J.; Kaplan, D. L., In vitro cartilage tissue engineering with 3D porous aqueous-derived silk scaffolds and mesenchymal stem cells. *Biomaterials* 2005, 26 (34), 7082-7094.
12. Jin, H. J.; Park, J.; Karageorgiou, V.; Kim, U. J.; Valluzzi, R.; Cebe, P.; Kaplan, D. L., Water-stable silk films with reduced β-sheet content. *Advanced Functional Materials* 2005, 15 (8), 1241-1247.
13. Karageorgiou, V.; Meinel, L.; Hofmann, S.; Malhotra, A.; Volloch, V.; Kaplan, D., Bone morphogenetic protein-2 decorated silk fibroin films induce osteogenic differentiation of human bone marrow stromal cells. *Journal of Biomedical Materials Research Part A: An Official Journal of The Society for Biomaterials, The Japanese Society for Biomaterials, and The Australian Society for Biomaterials and the Korean Society for Biomaterials* 2004, 71 (3), 528-537.
14. Choi, J.; McGill, M.; Raia, N. R.; Hasturk, O.; Kaplan, D. L., Silk Hydrogels Crosslinked by the Fenton Reaction. *Advanced healthcare materials* 2019, 8 (17), 1900644.
15. Chouhan, D.; Lohe, T. u.; Samudrala, P. K.; Mandal, B. B., In situ forming injectable silk fibroin hydrogel promotes skin regeneration in full thickness burn wounds. *Advanced healthcare materials* 2018, 7 (24), 1801092.
16. Hasturk, O.; Jordan, K. E.; Choi, J.; Kaplan, D. L., Enzymatically crosslinked silk and silk-gelatin hydrogels with tunable gelation kinetics, mechanical properties and bioactivity for cell culture and encapsulation. *Biomaterials* 2020, 232, 119720.
17. Kapoor, S.; Kundu, S. C., Silk protein-based hydrogels: promising advanced materials for biomedical applications. *Acta biomaterialia* 2016, 31, 17-32.
18. Barud, H. O.; Barud, H. d. S.; Cavicchioli, M.; do Amaral, T. S.; de Oliveira Junior, O. B.; Santos, D. M.; Petersen, A. L. d. O. A.; Celes, F.; Borges, V. M.; de Oliveira, C. I., Preparation and characterization of a bacterial cellulose/silk fibroin sponge scaffold for tissue regeneration. *Carbohydrate Polymers* 2015, 128, 41-51.
19. Liu, J.; Chen, H.; Wang, Y.; Li, G.; Zheng, Z.; Kaplan, D. L.; Wang, X.; Wang, X., Flexible Water-Absorbing Silk-Fibroin Biomaterial Sponges with Unique Pore Structure for Tissue Engineering. *ACS Biomaterials Science & Engineering* 2020, 6 (3), 1641-1649.
20. Sionkowska, A.; Planecka, A., Preparation and characterization of silk fibroin/chitosan composite sponges for tissue engineering. *Journal of Molecular Liquids* 2013, 178, 5-14.
21. Chirila, T. V.; Barnard, Z.; Harkin, D. G.; Schwab, I. R.; Hirst, L. W., *Bombyx mori* silk fibroin membranes as potential substrata for epithelial constructs used in the management of ocular surface disorders. *Tissue Engineering Part A* 2008, 14 (7), 1203-1211.
22. Karahaliloğlu, Z.; Ercan, B.; Denkbaş, E. B.; Webster, T. J., Nanofeatured silk fibroin membranes for dermal wound healing applications. *Journal of Biomedical Materials Research Part A* 2015, 103 (1), 135-144.
23. Cai, K.; Yao, K.; Cui, Y.; Yang, Z.; Li, X.; Xie, H.; Qing, T.; Gao, L., Influence of different surface modification treatments on poly (D, L-lactic acid) with silk fibroin and their effects on the culture of osteoblast in vitro. *Biomaterials* 2002, 23 (7), 1603-1611.
24. Cai, K.; Yao, K.; Lin, S.; Yang, Z.; Li, X.; Xie, H.; Qing, T.; Gao, L., Poly (D, L-lactic acid) surfaces modified by silk fibroin: effects on the culture of osteoblast in vitro. *Biomaterials* 2002, 23 (4), 1153-1160.
25. Varki, A., Biological roles of oligosaccharides: all of the theories are correct. *Glycobiology* 1993, 3 (2), 97-130.
26. Sears, P.; Wong, C.-H., Intervention of carbohydrate recognition by proteins and nucleic acids. *Proceedings of the National Academy of Sciences* 1996, 93 (22), 12086-12093.
27. Köwitsch, A.; Zhou, G.; Groth, T., Medical application of glycosaminoglycans: a review. *Journal of tissue engineering and regenerative medicine* 2018, 12 (1), e23-e41.
28. Amorim, S.; Reis, C. A.; Reis, R. L.; Pires, R. A., Extracellular Matrix Mimics Using Hyaluronan-Based Biomaterials. *Trends in Biotechnology* 2020.
29. Suo, H.; Li, L.; Zhang, C.; Yin, J.; Xu, K.; Liu, J.; Fu, J., Glucosamine-grafted methacrylated gelatin hydrogels as potential biomaterials for cartilage repair. *Journal of Biomedical Materials Research Part B: Applied Biomaterials* 2020, 108 (3), 990-999.
30. Raia, N. R.; Jia, D.; Ghezzi, C. E.; Muthukumar, M.; Kaplan, D. L., Characterization of silk-hyaluronic acid composite hydrogels towards vitreous humor substitutes. *Biomaterials* 2020, 233, 119729.
31. Chen, Q.; Shao, X.; Ling, P.; Liu, F.; Han, G.; Wang, F., Recent advances in polysaccharides for osteoarthritis therapy. *European Journal of Medicinal Chemistry* 2017, 139, 926-935.
32. Ting, S. S.; Chen, G.; Stenzel, M. H., Synthesis of glycopolymers and their multivalent recognitions with lectins. *Polymer Chemistry* 2010, 1 (9), 1392-1412.
33. Ladmiral, V.; Melia, E.; Haddleton, D. M., Synthetic glycopolymers: an overview. *European Polymer Journal* 2004, 40 (3), 431-449.
34. Miura, Y., Synthesis and biological application of glycopolymers. *Journal of Polymer Science Part A: Polymer Chemistry* 2007, 45 (22), 5031-5036.
35. Miura, Y.; Hoshino, Y.; Seto, H., Glycopolymer nanobiotechnology. *Chemical Reviews* 2016, 116 (4), 1673-1692.
36. Huang, X.; Huang, X. J.; Yu, A. G.; Wang, C.; Dai, Z. W.; Xu, Z. K., "Click Chemistry" as a Facile Approach to the Synthesis of Polyphosphazene Glycopolymers. *Macromolecular Chemistry and Physics* 2011, 212 (3), 272-277.
37. Ladmiral, V.; Mantovani, G.; Clarkson, G. J.; Cauet, S.; Irwin, J. L.; Haddleton, D. M., Synthesis of neoglycopolymers by a combination of "click chemistry" and living radical polymerization. *Journal of the American Chemical Society* 2006, 128 (14), 4823-4830.
38. Baldwin, A. D.; Kiick, K. L., Polysaccharide-modified synthetic polymeric biomaterials. *Peptide Science: Original Research on Biomolecules* 2010, 94 (1), 128-140.
39. Shu, X. Z.; Liu, Y.; Palumbo, F. S.; Luo, Y.; Prestwich, G. D., In situ crosslinkable hyaluronan hydrogels for tissue engineering. *Biomaterials* 2004, 25 (7-8), 1339-1348.

40. Flynn, L.; Prestwich, G. D.; Semple, J. L.; Woodhouse, K. A., Adipose tissue engineering with naturally derived scaffolds and adipose-derived stem cells. *Biomaterials* 2007, 28 (26), 3834-3842.
41. Lee, H.; Ahn, C. H.; Park, T. G., Poly [lactic-co-(glycolic acid)]-grafted hyaluronic acid copolymer micelle nanoparticles for target-specific delivery of doxorubicin. *Macromolecular Bioscience* 2009, 9 (4), 336-342.
42. Wang, D.-A.; Varghese, S.; Sharma, B.; Strehin, I.; Fermanian, S.; Gorham, J.; Fairbrother, D. H.; Cascio, B.; Elisseeff, J. H., Multifunctional chondroitin sulphate for cartilage tissue-biomaterial integration. *Nature materials* 2007, 6 (5), 385-392.
43. Benoit, D. S.; Anseth, K. S., Heparin functionalized PEG gels that modulate protein adsorption for hMSC adhesion and differentiation. *Acta biomaterialia* 2005, 1 (4), 461-470.
44. Yang, Y. J.; Holmberg, A. L.; Olsen, B. D., Artificially engineered protein polymers. *Annual Review of Chemical and Biomolecular Engineering* 2017, 8, 549-575.
45. Sionkowska, A., Current research on the blends of natural and synthetic polymers as new biomaterials. *Progress in polymer science* 2011, 36 (9), 1254-1276.
46. Gotoh, Y.; Niimi, S.; Hayakawa, T.; Miyashita, T., Preparation of lactose-silk fibroin conjugates and their application as a scaffold for hepatocyte attachment. *Biomaterials* 2004, 25 (6), 1131-1140.
47. Gotoh, Y.; Tsukada, M.; Aiba, S.-i.; Minoura, N., Chemical modification of silk fibroin with N-acetyl-chito-oligosaccharides. *International journal of biological macromolecules* 1996, 18 (1-2), 19-26.
48. Gotoh, Y.; Minoura, N.; Miyashita, T., Preparation and characterization of conjugates of silk fibroin and chitooligosaccharides. *Colloid and Polymer Science* 2002, 280 (6), 562-568.
49. Acharya, C.; Hinz, B.; Kundu, S. C., The effect of lactose-conjugated silk biomaterials on the development of fibrogenic fibroblasts. *Biomaterials* 2008, 29 (35), 4665-4675.
50. Yuan, J.; Zhou, Q.; Wang, P.; Deng, C.; Yuan, J.; Wang, Q., Phosphorylation of Silk Fibroin via Maillard Reaction and Its Behavior of Biomimetic Mineralization. *Fibers and Polymers* 2019, 20 (8), 1616-1623.
51. Pavlovic, E.; Serban, M. A.; Yu, X.; Manesis, N. J., Cross-linked silk-hyaluronic acid compositions. Google Patents: 2014.
52. Raia, N. R.; Partlow, B. P.; McGill, M.; Kimmerling, E. P.; Ghezzi, C. E.; Kaplan, D. L., Enzymatically cross-linked silk-hyaluronic acid hydrogels. *Biomaterials* 2017, 131, 58-67.
53. Vidal, S. E. L.; Tamamoto, K. A.; Nguyen, H.; Abbott, R. D.; Cairns, D. M.; Kaplan, D. L., 3D biomaterial matrix to support long term, full thickness, immunocompetent human skin equivalents with nervous system components. *Biomaterials* 2019, 198, 194-203.
54. Sundarakrishnan, A.; Zukas, H.; Coburn, J.; Bertini, B. T.; Liu, Z.; Georgakoudi, I.; Baugh, L.; Dasgupta, Q.; Black, L. D.; Kaplan, D. L., Bioengineered in vitro tissue model of fibroblast activation for modeling pulmonary fibrosis. *ACS Biomaterials Science & Engineering* 2019, 5 (5), 2417-2429.
55. Tanaka, K.; Kajiyama, N.; Ishikura, K.; Waga, S.; Kikuchi, A.; Ohtomo, K.; Takagi, T.; Mizuno, S., Determination of the site of disulfide linkage between heavy and light chains of silk fibroin produced by *Bombyx mori. Biochimica et Biophysica Acta (BBA)-Protein Structure and Molecular Enzymology* 1999, 1432 (1), 92-103.
56. Zhou, C. Z.; Confalonieri, F.; Jacquet, M.; Perasso, R.; Li, Z. G.; Janin, J., Silk fibroin: structural implications of a remarkable amino acid sequence. *Proteins: Structure, Function, and Bioinformatics* 2001, 44 (2), 119-122.
57. Copey, L.; Jean-Gérard, L.; Andrioletti, B.; Framery, E., Synthesis of P-stereogenic secondary phosphine oxides using α-d-glucosamine as a chiral precursor. *Tetrahedron Letters* 2016, 57 (5), 543-545.
58. Islam, S.; Bhuiyan, M. R.; Islam, M., Chitin and chitosan: structure, properties and applications in biomedical engineering. *Journal of Polymers and the Environment* 2017, 25 (3), 854-866.
59. Jamialahmadi, K.; Arasteh, O.; Riahi, M. M.; Mehri, S.; Riahi-Zanjani, B.; Karimi, G., Protective effects of glucosamine hydrochloride against free radical-induced erythrocytes damage. *Environmental Toxicology and Pharmacology* 2014, 38 (1), 212-219.
60. Serban, M. A.; Kaplan, D. L., pH-Sensitive ionomeric particles obtained via chemical conjugation of silk with poly (amino acid) s. *Biomacromolecules* 2010, 11 (12), 3406-3412.
61. Hasturk, O.; Sahoo, J. K.; Kaplan, D. L., Synthesis and characterization of silk ionomers for layer-by-layer electrostatic deposition on individual mammalian cells. *Biomacromolecules* 2020.
62. Murphy, A. R.; John, P. S.; Kaplan, D. L., Modification of silk fibroin using diazonium coupling chemistry and the effects on hMSC proliferation and differentiation. *Biomaterials* 2008, 29 (19), 2829-2838.
63. Sahoo, J. K.; Choi, J.; Hasturk, O.; Laubach, I.; Descoteaux, M. L.; Mosurkal, S.; Wang, B.; Zhang, N.; Kaplan, D. L., Silk degumming time controls horseradish peroxidase-catalyzed hydrogel properties. *Biomaterials Science* 2020.
64. Bertuzzi, D. L.; Becher, T. B.; Capreti, N. M.; Amorim, J.; Jurberg, I. D.; Megiatto Jr, J. D.; Ornelas, C., General Protocol to Obtain D-Glucosamine from Biomass Residues: Shrimp Shells, Cicada Sloughs and Cockroaches. *Global Challenges* 2018, 2 (11), 1800046.
65. Gouvion, C.; Mazeau, K.; Heyraud, A.; Taravel, F. R.; Tvaroska, I., Conformational study of digalacturonic acid and sodium digalacturonate in solution. *Carbohydrate research* 1994, 261 (2), 187-202.
66. Roda, A.; Sabatini, L.; Barbieri, A.; Guardigli, M.; Locatelli, M.; Violante, F. S.; Rovati, L. C.; Persiani, S., Development and validation of a sensitive HPLC-ESI-MS/MS method for the direct determination of glucosamine in human plasma. *Journal of Chromatography B* 2006, 844 (1), 119-126.
67. Lu, Q.; Huang, Y.; Li, M.; Zuo, B.; Lu, S.; Wang, J.; Zhu, H.; Kaplan, D. L., Silk fibroin electrogelation mechanisms. *Acta biomaterialia* 2011, 7 (6), 2394-2400.
68. Lu, Q.; Hu, X.; Wang, X.; Kluge, J. A.; Lu, S.; Cebe, P.; Kaplan, D. L., Water-insoluble silk films with silk I structure. *Acta biomaterialia* 2010, 6 (4), 1380-1387.
69. Koh, L.-D.; Cheng, Y.; Teng, C.-P.; Khin, Y.-W.; Loh, X.-J.; Tee, S.-Y.; Low, M.; Ye, E.; Yu, H.-D.; Zhang, Y.-W., Structures, mechanical properties and applications of silk fibroin materials. *Progress in Polymer Science* 2015, 46, 86-110.
70. Guo, C.; Li, C.; Vu, H. V.; Hanna, P.; Lechtig, A.; Qiu, Y.; Mu, X.; Ling, S.; Nazarian, A.; Lin, S. J., Thermoplastic moulding of regenerated silk. *Nature Materials* 2020, 19 (1), 102-108.

71. Liang, C. X.; Hirabayashi, K., Influence of solvation temperature on the molecular features and physical properties of fibroin membrane. *Polymer* 1992, 33 (20), 4388-4393.
72. Hu, X.; Kaplan, D.; Cebe, P., Determining beta-sheet crystallinity in fibrous proteins by thermal analysis and infrared spectroscopy. *Macromolecules* 2006, 39 (18), 6161-6170.
73. Sofia, S.; McCarthy, M. B.; Gronowicz, G.; Kaplan, D. L., Functionalized silk-based biomaterials for bone formation. *Journal of Biomedical Materials Research: An Official Journal of The Society for Biomaterials and The Japanese Society for Biomaterials* 2001, 54 (1), 139-148.
74. Minoura, N.; Aiba, S. I.; Gotoh, Y.; Tsukada, M.; Imai, Y., Attachment and growth of cultured fibroblast cells on silk protein matrices. *Journal of biomedical materials research* 1995, 29 (10), 1215-1221.
75. Meinel, L.; Fajardo, R.; Hofmann, S.; Langer, R.; Chen, J.; Snyder, B.; Vunjak-Novakovic, G.; Kaplan, D., Silk implants for the healing of critical size bone defects. *Bone* 2005, 37 (5), 688-698.
76. Tsukada, M.; Freddi, G.; Minoura, N.; Allara, G., Preparation and application of porous silk fibroin materials. *Journal of Applied Polymer Science* 1994, 54 (4), 507-514.
77. Kundu, B.; Rajkhowa, R.; Kundu, S. C.; Wang, X., Silk fibroin biomaterials for tissue regenerations. *Advanced drug delivery reviews* 2013, 65 (4), 457-470.
78. Wang, Y.; Kim, H.-J.; Vunjak-Novakovic, G.; Kaplan, D. L., Stem cell-based tissue engineering with silk biomaterials. *Biomaterials* 2006, 27 (36), 6064-6082.
79. Lawrence, B. D.; Marchant, J. K.; Pindrus, M. A.; Omenetto, F. G.; Kaplan, D. L., Silk film biomaterials for cornea tissue engineering. *Biomaterials* 2009, 30 (7), 1299-1308.
80. Rnjak-Kovacina, J.; Wray, L. S.; Burke, K. A.; Torregrosa, T.; Golinski, J. M.; Huang, W.; Kaplan, D. L., Lyophilized silk sponges: a versatile biomaterial platform for soft tissue engineering. *ACS biomaterials science & engineering* 2015, 1 (4), 260-270.
81. Andrade, F. K.; Alexandre, N.; Amorim, I.; Gartner, F.; Mauricio, A. C.; Luís, A. L.; Gama, M., Studies on the biocompatibility of bacterial cellulose. *Journal of bioactive and compatible polymers* 2013, 28 (1), 97-112.
82. Huettner, N.; Dargaville, T. R.; Forget, A., Discovering cell-adhesion peptides in tissue engineering: beyond RGD. *Trends in biotechnology* 2018, 36 (4), 372-383.
83. Cheng, F.; Wu, Y.; Li, H.; Yan, T.; Wei, X.; Wu, G.; He, J.; Huang, Y., Biodegradable N, O-carboxymethyl chitosan/oxidized regenerated cellulose composite gauze as a barrier for preventing postoperative adhesion. *Carbohydrate polymers* 2019, 207, 180-190.
84. Merle, M.; Lallemand, B.; Lim, A.; Gantois, G., Experimental and clinical evaluation of an absorbable biomaterial inducing an anti-adhesive barrier (Divide®). *European Journal of Orthopaedic Surgery & Traumatology* 2008, 18 (4), 255-263.
85. Hoshi, R. A.; Van Lith, R.; Jen, M. C.; Allen, J. B.; Lapidos, K. A.; Ameer, G., The blood and vascular cell compatibility of heparin-modified ePTFE vascular grafts. *Biomaterials* 2013, 34 (1), 30-41.
86. Kara, F.; Aksoy, E. A.; Calamak, S.; Hasirci, N.; Aksoy, S, Immobilization of heparin on chitosan-grafted polyurethane films to enhance anti-adhesive and antibacterial properties. *Journal of Bioactive and Compatible Polymers* 2016, 31 (1), 72-90.
87. McLean, K. M.; Johnson, G.; Chatelier, R. C.; Beumer, G. J.; Steele, J. G.; Griesser, H. J., Method of immobilization of carboxymethyl-dextran affects resistance to tissue and cell colonization. *Colloids and surfaces B: biointerfaces* 2000, 18 (3-4), 221-234.
88. Velzenberger, E.; Vayssade, M.; Legeay, G.; Nagel, M.-D., Study of cell behaviour on a cellulose anti-adhesive substratum. *Cellulose* 2008, 15 (2), 347-357.
89. Chaturvedi, A. A.; Lomme, R. M.; Hendriks, T.; van Goor, H., Ultrapure alginate anti-adhesion gel does not impair colon anastomotic strength. *journal of surgical research* 2014, 192 (2), 432-439.
90. El Khoury, J.; Thomas, C. A.; Loike, J. D.; Hickman, S. E.; Cao, L.; Silverstein, S. C., Macrophages adhere to glucose-modified basement membrane collagen IV via their scavenger receptors. *Journal of Biological Chemistry* 1994, 269 (14), 10197-10200.
91. Kim, S.-H.; Goto, M.; Akaike, T., Specific binding of glucose-derivatized polymers to the asialoglycoprotein receptor of mouse primary hepatocytes. *Journal of Biological Chemistry* 2001, 276 (38), 35312-35319.
92. Zhu, K.; Amin, M. A.; Kim, M. J.; Katschke, K. J.; Park, C. C.; Koch, A. E., A novel function for a glucose analog of blood group H antigen as a mediator of leukocyte-endothelial adhesion via intracellular adhesion molecule 1. *Journal of Biological Chemistry* 2003, 278 (24), 21869-21877.
93. Rockwood, D. N.; Preda, R. C.; Yücel, T.; Wang, X.; Lovett, M. L.; Kaplan, D. L., Materials fabrication from Bombyx mori silk fibroin. *Nature protocols* 2011, 6 (10), 1612.
94. McGill, M.; Coburn, J. M.; Partlow, B. P.; Mu, X.; Kaplan, D. L., Molecular and macro-scale analysis of enzyme-crosslinked silk hydrogels for rational biomaterial design. *Acta biomaterialia* 2017, 63, 76-84.

We claim:

1. A composition comprising a saccharide-substituted silk fibroin, the saccharide-substituted silk fibroin comprising at least one saccharide covalently coupled to silk fibroin via a serine residue on the silk fibroin, wherein the serine residue is modified by carboxylation, wherein the at least one saccharide has an amine group and is selected from the group consisting of a monosaccharide, a disaccharide, and an oligosaccharide, and wherein a linking agent covalently couples the modified serine residue to the amine group of the at least one saccharide.

2. The composition of claim 1, wherein the at least one saccharide is glucosamine.

3. The composition of claim 1, wherein a total amount of serine residues covalently coupled to the at least one saccharide ranges from 0.1 to 12.1 mol %, based on the total amount of moles in the saccharide-substituted silk fibroin.

4. The composition of claim 3, wherein the total amount of serine residues covalently coupled to the at least one saccharide is at least 1 mol %, at least 2 mol %, at least 3 mol %, at least 4 mol %, or at least 5 mol %, based on the total amount of moles in the saccharide-substituted silk fibroin.

5. The composition of claim 1, wherein the linking agent is a carboxyalkyl halogen compound.

6. The composition of claim 1, wherein the saccharide-substituted silk fibroin is formed by contacting the silk fibroin with the at least one saccharide in a presence of 1-ethyl-3-(-3-dimethylaminopropyl) carbodiimide hydrochloride and N-hydroxysuccinimide.

7. The composition of claim 1, further comprising:
   (i) at least one threonine substitution, wherein at least a second saccharide is covalently coupled to the silk fibroin via a threonine residue, and wherein the threonine residue is modified by carboxylation;
(ii) at least one aspartic acid substitution, wherein at least a third saccharide is covalently coupled to the silk fibroin via an aspartic acid residue;
(iii) at least one glutamic acid substitution, wherein at least a fourth saccharide is covalently coupled to the silk fibroin via a glutamic acid residue; or
(iv) a combination thereof.

8. The composition of claim 1, further comprising at least one unsubstituted tyrosine residue.

9. The composition of claim 8, wherein the at least one unsubstituted tyrosine residue is present in an amount from 0.01 to 5.3 mol %, based on a total amount of moles in the saccharide-substituted silk fibroin.

10. The composition of claim 1, wherein the at least one saccharide is present in the saccharide-substituted silk fibroin in an amount from 0.01 to 0.18 mM.

11. The composition of claim 1, wherein the saccharide-substituted silk fibroin has a molecular weight from 50 kDa to 120 kDa.

12. The composition of claim 1, wherein the saccharide-substituted silk fibroin has a molecular weight from 120 kDa to 300 kDa.

13. The composition of claim 1, wherein the saccharide-substituted silk fibroin is in a form of a film, a hydrogel, or a sponge.

14. The composition of claim 1, wherein the saccharide-substituted silk fibroin has a water contact angle from 35 to 40 degrees.

15. The composition of claim 1, wherein a surface of the saccharide-substituted silk fibroin is characterized as having a dye reduction percentage of less than 1% after 24 hours following positioning cells on the surface at a cell density of at least 8000 cell/cm$^2$ in a growth medium.

16. The composition of claim 15, wherein the dye reduction percentage is less than 1% after 8 days following positioning the cells on the surface.

17. A composition comprising a saccharide-substituted silk fibroin, the saccharide-substituted silk fibroin comprising at least one saccharide covalently coupled to silk fibroin via an aspartic acid residue and/or a glutamic acid residue on the silk fibroin, wherein the at least one saccharide has an amine group and is selected from the group consisting of a monosaccharide, a disaccharide, and an oligosaccharide, and wherein a linking agent covalently couples the aspartic acid residue and/or the glutamic acid residue to the amine group of the at least one saccharide.

18. A composition comprising a saccharide-substituted silk fibroin, the saccharide-substituted silk fibroin comprising at least one saccharide covalently coupled to silk fibroin via a tyrosine residue on the silk fibroin, wherein the tyrosine residue is modified by conjugating with diazonium, wherein the at least one saccharide has an amine group and is selected from the group consisting of a monosaccharide, a disaccharide, and an oligosaccharide, and wherein a linking agent covalently couples the modified tyrosine residue to the amine group of the at least one saccharide.

* * * * *